(12) United States Patent
Kusner et al.

(10) Patent No.: US 10,093,963 B2
(45) Date of Patent: Oct. 9, 2018

(54) SYSTEM AND METHOD FOR PROCESSING BIOLOGICAL SAMPLES

(71) Applicant: NeuMoDx Molecular, Inc., Ann Arbor, MI (US)

(72) Inventors: Michael T. Kusner, Ann Arbor, MI (US); Jeffrey Williams, Ann Arbor, MI (US)

(73) Assignee: NeuMoDx Molecular, Inc., Ann Arbor, MI (US)

( * ) Notice: Subject to any disclaimer, the term of this patent is extended or adjusted under 35 U.S.C. 154(b) by 0 days.

(21) Appl. No.: 15/465,796

(22) Filed: Mar. 22, 2017

(65) Prior Publication Data

US 2017/0191115 A1    Jul. 6, 2017

Related U.S. Application Data

(63) Continuation of application No. 14/229,396, filed on Mar. 28, 2014, now Pat. No. 9,637,775, which is a (Continued)

(51) Int. Cl.
*C12Q 1/6806* (2018.01)
*B01L 3/00* (2006.01)
(Continued)

(52) U.S. Cl.
CPC ...... *C12Q 1/6806* (2013.01); *B01L 3/502715* (2013.01); *B01L 3/502738* (2013.01);
(Continued)

(58) Field of Classification Search
CPC ....... B29C 66/71; B29C 65/08; B29C 65/606; B29C 66/81423; B29C 66/8322;
(Continued)

(56) References Cited

U.S. PATENT DOCUMENTS 776,747 A    12/1904  Kling
778,036 A    12/1904  Hepp et al.
(Continued)

FOREIGN PATENT DOCUMENTS

CN    101432698    5/2009
CN      1773190    5/2010
(Continued)

OTHER PUBLICATIONS

Compton, Cancer and Metastasis Rev., vol. 11, pp. 105-119 (1992).

*Primary Examiner* — Nathan A Bowers
*Assistant Examiner* — Lydia Edwards
(74) *Attorney, Agent, or Firm* — Jeffrey Schox

(57) ABSTRACT

A system and method for processing and detecting nucleic acids from a set of biological samples, comprising: a molecular diagnostic module configured to receive nucleic acids bound to magnetic beads, isolate nucleic acids, and analyze nucleic acids, comprising a cartridge receiving module, a heating/cooling subsystem and a magnet configured to facilitate isolation of nucleic acids, a valve actuation subsystem including an actuation substrate, and a set of pins interacting with the actuation substrate, and a spring plate configured to bias at least one pin in a configurations, the valve actuation subsystem configured to control fluid flow through a microfluidic cartridge for processing nucleic acids, and an optical subsystem for analysis of nucleic acids; and a fluid handling system configured to deliver samples and reagents to components of the system to facilitate molecular diagnostic protocols.

20 Claims, 11 Drawing Sheets

Related U.S. Application Data continuation-in-part of application No. 13/766,359, filed on Feb. 13, 2013, now Pat. No. 9,050,594.

(60) Provisional application No. 61/667,606, filed on Jul. 3, 2012, provisional application No. 61/598,240, filed on Feb. 13, 2012.

(51) Int. Cl.
   *F16K 99/00* (2006.01)
   *B01L 99/00* (2010.01)

(52) U.S. Cl.
   CPC ..... *F16K 99/0005* (2013.01); *B01L 2200/025* (2013.01); *B01L 2200/027* (2013.01); *B01L 2200/0631* (2013.01); *B01L 2200/10* (2013.01); *B01L 2300/0654* (2013.01); *B01L 2300/0681* (2013.01); *B01L 2300/087* (2013.01); *B01L 2300/123* (2013.01); *F16K 2099/0084* (2013.01)

(58) Field of Classification Search
   CPC ......... B29K 2021/00; B01L 2200/0684; B01L 2200/0689; B01L 2200/10; B01L 2300/1827; B01L 2400/0487; B01L 2400/0655; B01L 3/5027

See application file for complete search history.

(56) References Cited

U.S. PATENT DOCUMENTS

| | | |
|---|---|---|
| 3,963,151 A | 6/1976 | North, Jr. |
| 5,681,529 A | 10/1997 | Taguchi et al. |
| 5,725,831 A | 3/1998 | Reichler et al. |
| 5,750,338 A | 5/1998 | Collins et al. |
| 5,783,148 A | 7/1998 | Cottingham et al. |
| 5,824,478 A | 10/1998 | Muller |
| 5,853,667 A | 12/1998 | Seaton et al. |
| 6,168,948 B1 | 1/2001 | Anderson et al. |
| 6,331,266 B1 | 12/2001 | Powell et al. |
| 6,368,871 B1 | 4/2002 | Christel et al. |
| 6,374,684 B1 | 4/2002 | Dority |
| 6,374,685 B1 | 4/2002 | Daly |
| 6,431,476 B1 | 8/2002 | Taylor et al. |
| 6,440,725 B1 | 8/2002 | Pourahmadi et al. |
| 6,664,104 B2 | 12/2003 | Pourahmadi et al. |
| 6,692,700 B2 | 2/2004 | Handique |
| 6,852,287 B2 | 2/2005 | Ganesan |
| 6,860,993 B2 | 3/2005 | Effenhauser et al. |
| 6,872,315 B2 | 3/2005 | Effenhauser et al. |
| 6,878,540 B2 | 4/2005 | Pourahmadi et al. |
| 6,887,693 B2 | 5/2005 | McMillan et al. |
| 6,893,879 B2 | 5/2005 | Petersen et al. |
| 6,899,838 B2 | 5/2005 | Lastovich |
| 6,987,018 B2 | 1/2006 | Taylor et al. |
| 7,052,268 B2 | 5/2006 | Powell et al. |
| 7,135,144 B2 | 11/2006 | Christel et al. |
| 7,186,383 B2 | 3/2007 | Webster et al. |
| 7,192,557 B2 | 3/2007 | Wu et al. |
| 7,252,501 B2 | 8/2007 | Pruden et al. |
| 7,270,786 B2 | 9/2007 | Parunak et al. |
| 7,323,140 B2 | 1/2008 | Handique et al. |
| 7,332,130 B2 | 2/2008 | Handique |
| 7,372,616 B2 | 5/2008 | Bang et al. |
| 7,445,901 B2 | 11/2008 | Kudlicki et al. |
| 7,473,397 B2 | 1/2009 | Griffin et al. |
| 7,556,858 B2 | 7/2009 | Rasmussen et al. |
| 7,569,346 B2 | 8/2009 | Petersen et al. |
| 7,580,533 B2 | 8/2009 | Schwartz |
| 7,666,681 B2 | 2/2010 | Ammann et al. |
| 7,674,431 B2 | 3/2010 | Ganesan |
| 7,682,820 B2 | 3/2010 | Bader |
| 7,704,735 B2 | 4/2010 | Facer et al. |
| 7,731,906 B2 | 6/2010 | Handique et al. |
| 7,738,094 B2 | 6/2010 | Goldberg |
| 7,763,209 B2 | 7/2010 | Haley |
| 7,767,447 B2 | 8/2010 | Breidenthal et al. |
| 7,820,030 B2 | 10/2010 | Althaus et al. |
| 7,863,035 B2 | 1/2011 | Clemens et al. |
| 7,906,758 B2 | 3/2011 | Stults et al. |
| 7,914,994 B2 | 3/2011 | Petersen et al. |
| 7,935,537 B2 | 5/2011 | Haley |
| 7,943,388 B2 | 5/2011 | Baetzold et al. |
| 7,955,798 B2 | 6/2011 | Mauritz |
| 7,955,864 B2 | 6/2011 | Cox et al. |
| 7,964,413 B2 | 6/2011 | Macioszek et al. |
| 7,987,022 B2 | 7/2011 | Handique et al. |
| 7,995,798 B2 | 8/2011 | Krupnik et al. |
| 7,998,708 B2 | 8/2011 | Handique et al. |
| 8,003,329 B2 | 8/2011 | Macevicz |
| 8,008,046 B2 | 8/2011 | Maltezos et al. |
| 8,008,066 B2 | 8/2011 | Lair et al. |
| 8,043,581 B2 | 10/2011 | Ganesan |
| 8,048,375 B2 | 11/2011 | Breidenthal et al. |
| 8,048,386 B2 | 11/2011 | Dority et al. |
| 8,052,929 B2 | 11/2011 | Breidenthal et al. |
| 8,057,446 B2 | 11/2011 | Kane et al. |
| 8,088,616 B2 | 1/2012 | Handique |
| 8,105,477 B2 | 1/2012 | Althaus et al. |
| 8,105,783 B2 | 1/2012 | Handique |
| 8,110,158 B2 | 2/2012 | Handique |
| 8,133,671 B2 | 3/2012 | Williams et al. |
| 625,544 A1 | 4/2012 | Radicke |
| 8,168,134 B2 | 5/2012 | Lehto |
| 8,182,763 B2 | 5/2012 | Duffy et al. |
| 8,183,359 B2 | 5/2012 | Becker et al. |
| 8,187,557 B2 | 5/2012 | Van Atta et al. |
| 8,247,176 B2 | 8/2012 | Petersen et al. |
| 8,248,597 B2 | 8/2012 | Goldberg |
| 8,268,245 B2 | 9/2012 | Wahl |
| 8,268,603 B2 | 9/2012 | Taylor et al. |
| 8,273,308 B2 | 9/2012 | Handique et al. |
| 8,287,820 B2 | 10/2012 | Williams et al. |
| 8,288,520 B2 | 10/2012 | Eder et al. |
| 8,323,584 B2 | 12/2012 | Ganesan |
| 8,323,899 B2 | 12/2012 | Sherman et al. |
| 8,323,900 B2 | 12/2012 | Handique et al. |
| 8,324,372 B2 | 12/2012 | Brahmasandra et al. |
| 8,349,564 B2 | 1/2013 | Macioszek et al. |
| 8,388,908 B2 | 3/2013 | Blaga et al. |
| 8,394,336 B2 | 3/2013 | Curcio |
| 8,404,198 B2 | 3/2013 | Amshey et al. |
| 8,414,845 B2 | 4/2013 | Chen et al. |
| 8,415,103 B2 | 4/2013 | Handique |
| 8,420,015 B2 | 4/2013 | Ganesan et al. |
| 8,431,413 B2 | 4/2013 | Dority et al. |
| 8,440,149 B2 | 5/2013 | Handique |
| 8,449,833 B2 | 5/2013 | Nieuwenhuis |
| 8,470,586 B2 | 6/2013 | Wu et al. |
| 8,470,588 B2 | 6/2013 | Boehm et al. |
| 8,473,104 B2 | 6/2013 | Handique et al. |
| 8,480,976 B2 | 7/2013 | Breidenthal et al. |
| 8,491,178 B2 | 7/2013 | Breidenthal et al. |
| 8,501,461 B2 | 8/2013 | Knight et al. |
| 8,506,908 B2 | 8/2013 | Benn et al. |
| 8,513,962 B2 | 8/2013 | Kiyokawa et al. |
| 8,640,555 B2 | 2/2014 | Zenhausern et al. |
| 8,642,787 B2 | 2/2014 | Fukushima et al. |
| 8,672,532 B2 | 3/2014 | Jovanovich et al. |
| 8,709,787 B2 | 4/2014 | Handique |
| 8,734,761 B2 | 5/2014 | Willard et al. |
| 8,738,106 B2 | 5/2014 | Rabinowitz et al. |
| 8,852,862 B2 | 10/2014 | Wu et al. |
| 9,040,288 B2 | 5/2015 | Handique et al. |
| 9,050,594 B2 | 6/2015 | Williams et al. |
| 9,101,930 B2 | 8/2015 | Williams et al. |
| 9,180,451 B2 | 11/2015 | Ziglioli et al. |
| 9,238,809 B2 | 1/2016 | Khripin et al. |
| 9,339,812 B2 | 5/2016 | Williams et al. |
| 9,382,532 B2 | 7/2016 | Brahmasandra et al. |
| 9,618,506 B2 | 4/2017 | Lowe et al. |
| 9,663,779 B2 | 5/2017 | Fabis et al. |
| 2002/0160518 A1 | 10/2002 | Hayenga et al. |

(56) References Cited

U.S. PATENT DOCUMENTS

| | | |
|---|---|---|
| 2003/0170686 A1 | 9/2003 | Hoet et al. |
| 2004/0018611 A1 | 1/2004 | Ward et al. |
| 2004/0138154 A1 | 7/2004 | Yu et al. |
| 2005/0205199 A1 | 9/2005 | Green |
| 2005/0250199 A1* | 11/2005 | Anderson ............ B01F 11/0071 435/287.2 |
| 2006/0182842 A1* | 8/2006 | Pruden ................ B29C 45/2806 425/568 |
| 2007/0184463 A1 | 8/2007 | Molho et al. |
| 2008/0057572 A1 | 3/2008 | Petersen et al. |
| 2008/0241569 A1 | 10/2008 | Qin et al. |
| 2008/0280285 A1 | 11/2008 | Chen et al. |
| 2009/0275014 A1* | 11/2009 | Maltezos ............ B01L 3/50851 435/5 |
| 2010/0009351 A1 | 1/2010 | Brahmasandra et al. |
| 2010/0029544 A1 | 2/2010 | Cheng et al. |
| 2010/0075311 A1 | 3/2010 | Barrault et al. |
| 2010/0300563 A1 | 12/2010 | Ramunas et al. |
| 2011/0003281 A1 | 1/2011 | Woudenberg et al. |
| 2011/0053289 A1* | 3/2011 | Lowe .................... B01L 3/5027 436/501 |
| 2011/0201099 A1 | 8/2011 | Anderson et al. |
| 2012/0046203 A1 | 2/2012 | Walsh et al. |
| 2013/0210015 A1* | 8/2013 | Williams ................. C12Q 1/68 435/6.12 |

FOREIGN PATENT DOCUMENTS

| | | |
|---|---|---|
| CN | 101842690 | 6/2013 |
| EP | 0707077 | 4/1996 |
| WO | 048164 | 6/2002 |
| WO | 003200 | 1/2004 |
| WO | 064635 | 6/2007 |
| WO | 097342 | 8/2008 |
| WO | 115626 | 9/2008 |
| WO | 022994 | 2/2009 |
| WO | 038536 | 3/2009 |
| WO | 072821 | 7/2010 |
| WO | 121315 | 10/2010 |

* cited by examiner

SYSTEM AND METHOD FOR PROCESSING BIOLOGICAL SAMPLES

CROSS-REFERENCE TO RELATED APPLICATIONS

This application is a continuation of U.S. application Ser. No. 14/229,396, filed 28 Mar. 2014, which is a continuation-in-part of U.S. application Ser. No. 13/766,359, filed 13 Feb. 2013, which claims the benefit of U.S. Provisional Application No. 61/667,606, filed 3 Jul. 2012 and U.S. Provisional Application No. 61/598,240, filed 13 Feb. 2012, all of which are incorporated herein in their entirety by this reference.

TECHNICAL FIELD

This invention relates generally to the molecular diagnostics field, and more specifically to an improved system and method for processing biological samples.

BACKGROUND

Molecular diagnostics is a clinical laboratory discipline that has developed rapidly during the last 25 years. It originated from basic biochemistry and molecular biology research procedures, but now has become an independent discipline focused on routine analysis of nucleic acids (NA), including deoxyribonucleic acid (DNA) and ribonucleic acid (RNA) for diagnostic use in healthcare and other fields involving analysis of nucleic acids of biological samples. Molecular diagnostic analysis of biological samples can include the detection of one or more nucleic acid materials present in a specimen. The particular analysis performed may be qualitative and/or quantitative. Methods of analysis typically involve isolation, purification, and amplification of nucleic acid materials, and polymerase chain reaction (PCR) is a common technique used to amplify nucleic acids. Often, a nucleic acid sample to be analyzed is obtained in insufficient quantity, quality, and/or purity, hindering a robust implementation of a diagnostic technique. Current sample processing methods and molecular diagnostic techniques are often labor/time intensive, low throughput, and expensive, and systems of analysis are insufficient. Furthermore, methods of isolation, processing, and amplification are specific to certain sample matrices and/or nucleic acid types and not applicable across common biological sample and nucleic acid types.

Due to these and other deficiencies of current molecular diagnostic systems and methods, there is thus a need for and improved system and method to facilitate processing of biological samples. This invention provides such a system and method.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. System for Processing and Detecting Nucleic Acids

Figure 1A:
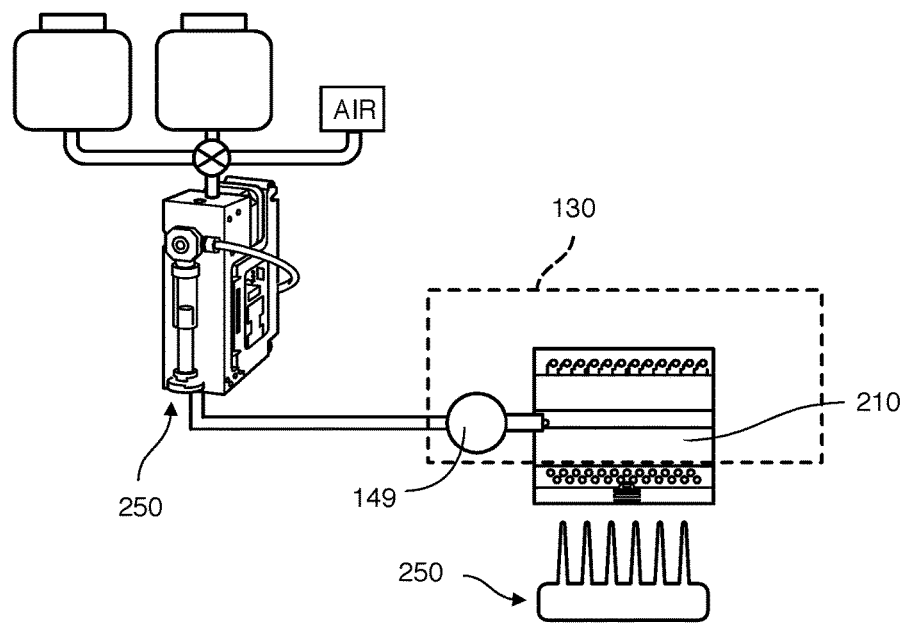
FIGS. 1A-1B depict an embodiment of a system for processing biological samples.
Figure 1B:
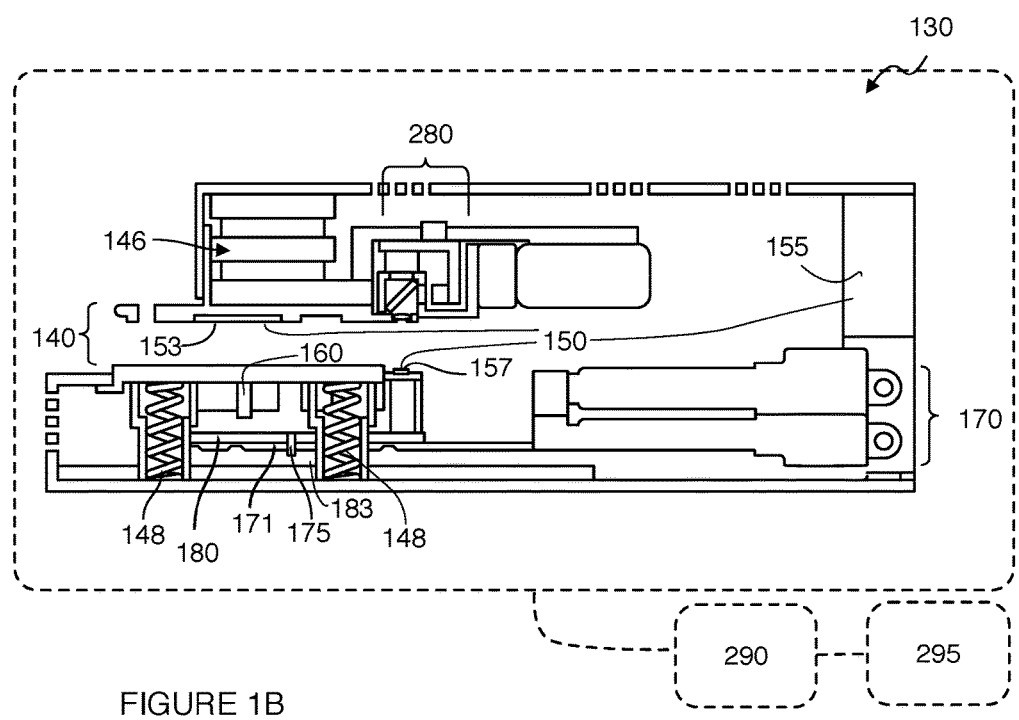

As shown in FIGS. 1A-1B, an embodiment of a system 100 for processing biological samples includes: a molecular diagnostic module 130 comprising a microfluidic cartridge receiving module 140, heating and cooling subsystem 150, a magnet 160, a valve actuation subsystem 170, and an optical subsystem 280. Other embodiments of the system 100 can further comprise a microfluidic cartridge 210 configured to facilitate sample processing; a liquid handling system 250 configured to facilitate gas and fluid delivery to different elements of the system 100; a processor 290 configured to analyze data resulting from a run of the system 100; and a user interface 295 configured to allow a user to interact with the system 100. The system 100 can additionally or alternatively include any other suitable elements, as described in U.S. application Ser. No. 13/766,359 entitled "System and Method for Processing and Detecting Nucleic Acids" and filed on 13 Feb. 2013, which is incorporated herein in its entirety by this reference. The system 100 thus functions to receive biological samples containing nucleic acids (i.e., impure nucleic acid samples), separate nucleic acids from the biological samples, and analyze nucleic acid samples according to at least one molecular diagnostic protocol (e.g., PCR). Preferably, the system 100 is a walk-away system by which a user loads a set of biological samples containing nucleic acids, and receives a set of data resulting from a molecular diagnostic protocol without any further sample manipulation by the user. Alternatively, the system 100 facilitates aspects of sample preparation for a molecular diagnostic protocol, with some sample manipulation performed by the user.

In one example workflow of the system 100, a liquid handling system 250 aspirates a set of biological samples and dispenses the biological samples into a microfluidic cartridge 210, aligned within a cartridge receiving module 140 of a molecular diagnostic module 130, and configured to be manipulated by the molecular diagnostic module 130. A heating and cooling subsystem 150, a magnet 160, and a valve actuation subsystem 170 of the molecular diagnostic module 130 then facilitate separation of a set of nucleic acids from the biological samples, as the liquid handling system 250 dispenses wash solutions, release solutions, and/or air at appropriate stages. The liquid handling system 250 then aspirates the set of nucleic acids from the microfluidic cartridge 210 contained within the molecular diagnostic module 130, combines the set of nucleic acids with a set of molecular diagnostic reagents, and dispenses the set of nucleic acids combined with the set of molecular diagnostic reagents (i.e., set of nucleic acid-reagent mixtures) into the microfluidic cartridge 210 within the molecular diagnostic module 130. The heating and cooling subsystem 150, optical subsystem 180 and valve actuation subsystem 170 of the molecular diagnostic module 130 then facilitate analysis of the set of nucleic acid-reagent mixtures by a processor configured to display information on a user interface.

As stated, the above workflow is just one example workflow of the system 100. A detailed description of elements of an embodiment of the system 100 is described in sections 1.1-1.4 below.

1.1 System—Molecular Diagnostic Module

As shown in FIG. 1B, an embodiment of the molecular diagnostic module 130 of the system 100 includes a cartridge receiving module 140, a heating and cooling subsystem 150, a magnet 160, a valve actuation subsystem 170, and an optical subsystem 280, and functions to manipulate a microfluidic cartridge 210 for processing of a biological sample containing nucleic acids. The molecular diagnostic module 130 is preferably configured to operate in parallel with at least one other molecular diagnostic module 130, such that multiple microfluidic cartridges 210 containing biological samples may be processed simultaneously. In a first variation, the molecular diagnostic module 130 is configured to be stackable with another molecular diagnostic module 130 in a manner that enables access to a microfluidic cartridge 210 within each molecular diagnostic module 130. In another variation, the molecular diagnostic module 130 may not be configured to stack with another molecular diagnostic module, such that the molecular diagnostic modules 130 are configured to rest side-by-side on the same plane. Elements of an embodiment of the molecular diagnostic module 130 are further described in sections 1.1.1 to 1.1.4 below.

1.1.1 Molecular Diagnostic Module—Cartridge Receiving Module

Figure 2:
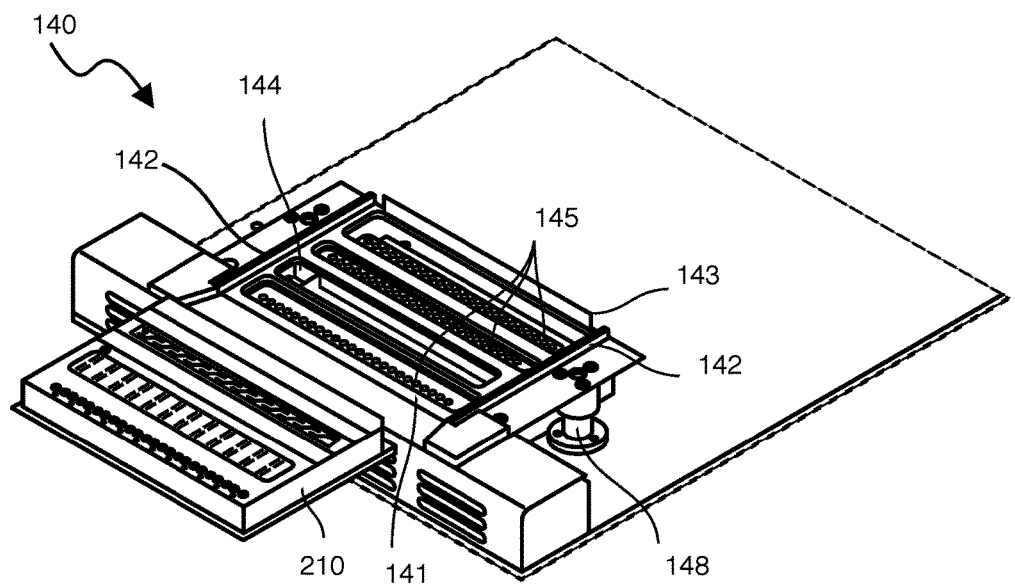
FIGS. 2-3 depict embodiments of a molecular diagnostic module for processing biological samples.
Figure 3:
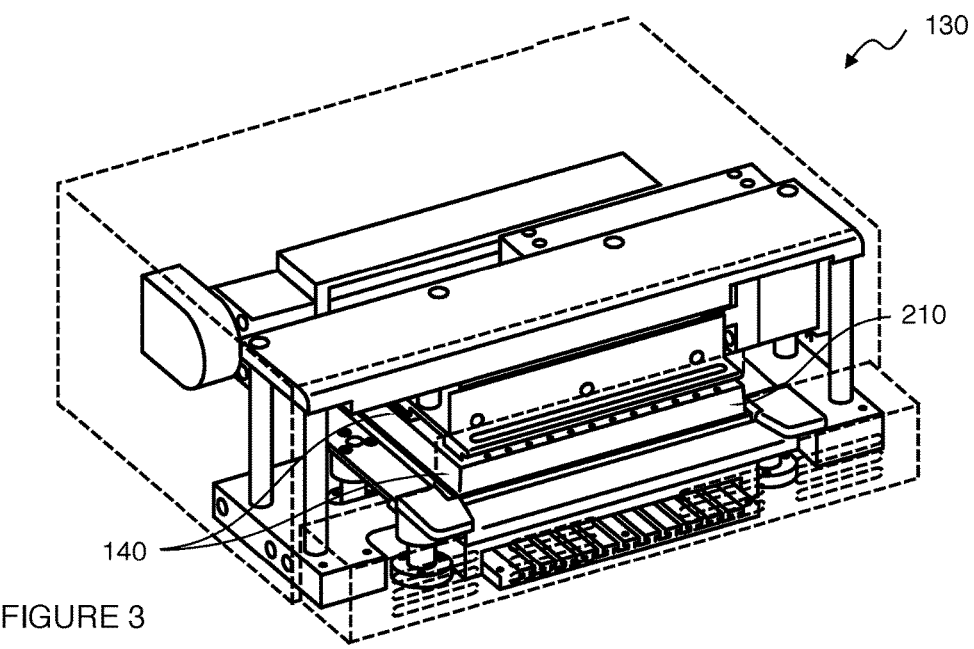

As shown in FIGS. 1B, 2, and 3, the cartridge receiving module 140 of the molecular diagnostic module 130 comprises a cartridge platform 141 including a cartridge loading guiderail 142, a cartridge stop 143, a magnet receiving slot 144, and a set of access regions 145; a linear actuator 146 configured to displace a microfluidic cartridge 210 resting on the cartridge platform 141; and a set of springs 148 coupled to the cartridge platform 141. The cartridge receiving module 140 thus functions to receive, align, and compress a microfluidic cartridge 210 for processing of a biological sample according to a molecular diagnostic assay protocol. The cartridge platform 141 is preferably configured to receive a microfluidic cartridge 210 along a cartridge loading guiderail 142 until it reaches a cartridge stop 143, and be vertically displaced by the linear actuator 146, which places a biasing force against the set of springs 148 coupled to the cartridge platform 141. The magnet receiving slot 144 and the set of access regions 145 provide access, by a magnet 160 and a valve actuation subsystem 170, to the microfluidic cartridge 210, as the microfluidic cartridge 210 is vertically displaced by the linear actuator 146.

The cartridge platform 141 includes a cartridge loading guiderail 142, a cartridge stop 143, a magnet receiving slot 144, and a set of access regions 145, and functions to receive and align a microfluidic cartridge 210, while providing access to the microfluidic cartridge 210 by a magnet 160 and a valve actuation subsystem 170. As shown in FIG. 2, an embodiment of the cartridge platform 141 includes a pair of parallel cartridge loading guiderails 142, initiating at a pair of inwardly tapering protrusions configured to guide a microfluidic cartridge toward the pair of parallel cartridge loading guiderails 142, and spanning two short edges of the cartridge platform 141. The embodiment of the cartridge platform 141 also includes a cartridge stop 143 comprising a vertical tab oriented perpendicular to the cartridge loading guiderails 142, and spanning a long edge of the cartridge platform. Preferably, the cartridge loading guiderails 142 and the cartridge stop 143 are configured such that a microfluidic cartridge 210 slides between the cartridge loading guiderails 142 and hits the cartridge stop 143 to signal proper alignment. Alternatively, the cartridge loading guiderails 142 and the cartridge stop 143 can be configured such that a microfluidic cartridge slides over or along the cartridge loading guiderails 142, after which the cartridge stop 143 couples to a portion of the microfluidic cartridge 210 to ensure proper alignment of the microfluidic cartridge. Additional variations of the cartridge loading guiderails 142 and the cartridge stop 143 can be used to enable reception and alignment of a microfluidic cartridge 210 by the molecular diagnostic module 130.

The embodiment of the cartridge platform 141 shown in FIG. 2 also includes a set of access regions 145, oriented perpendicular to the parallel cartridge loading guiderails 142 and configured to provide access to a valve actuation subsystem 170, and a magnet receiving slot 144 located among the set of access regions 145. Preferably, the magnet receiving slot 144 and the set of access regions 145 substantially span a long dimension of the cartridge platform 141, as shown in FIG. 2, and are configured to correspond to locations on a microfluidic cartridge 210 requiring a magnetic field and/or valving to enable processing of a biological sample and nucleic acid detection once the microfluidic cartridge 210 has been aligned within the molecular diagnostic module 130. Thus, alternative configurations of the magnet receiving slot 144 and the set of access regions 145 can accommodate other cartridges with alternative regions requiring magnetic fields and/or valving to enable other protocols. In one alternative embodiment, the magnet receiving slot 144 and the access regions can comprise one continuous void of the cartridge platform 141, such that the cartridge platform 141 supports a microfluidic cartridge 210 along the periphery of the microfluidic cartridge 210, but forms a continuous void under a majority of the footprint of the microfluidic cartridge 210.

Figure 4A:
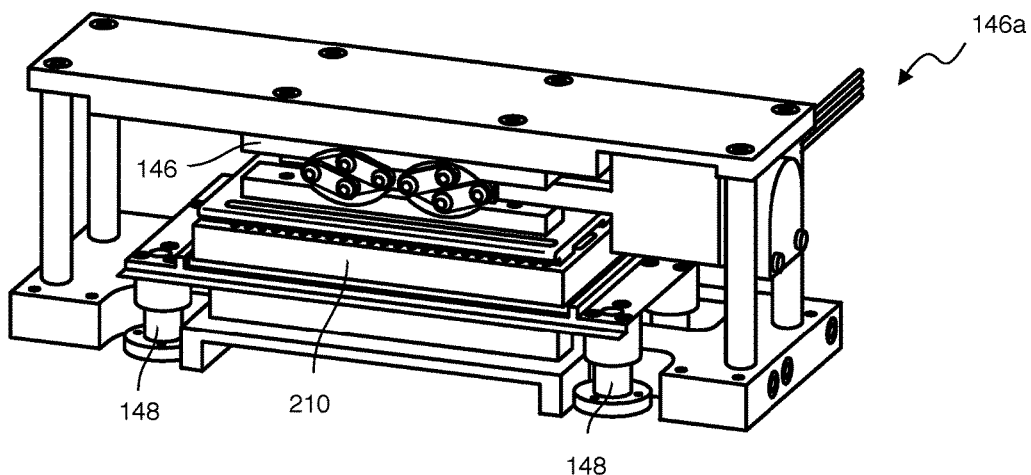
FIGS. 4A-4B depict configurations of a linear actuator of an embodiment of a molecular diagnostic module.
Figure 4B:
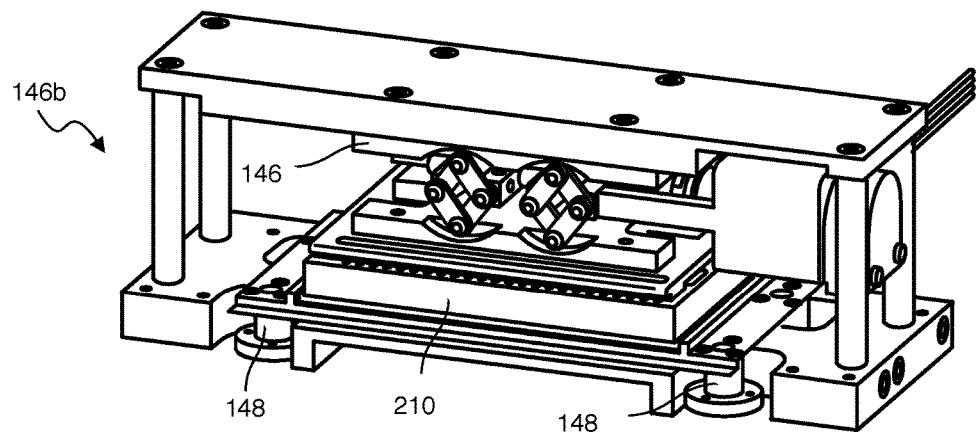

The linear actuator 146 functions to linearly displace a microfluidic cartridge 210 resting on the cartridge platform 141, in order to compress the microfluidic cartridge 210 and position the microfluidic cartridge 210 between a cartridge heater 153 and an optical subsystem 280 on one side of the microfluidic cartridge 210, and a magnet 160 and detection chamber heaters 157 on another side of the microfluidic cartridge 210, as described in further detail below. The linear actuator 146 also functions to provide a sufficient counterforce to the valve actuation subsystem 170 such that a microfluidic cartridge 210 within the molecular diagnostic module 130 remains properly situation upon manipulation by the valve actuation subsystem 170. The linear actuator 146 further functions to move a nozzle 149 coupled to the liquid handling system 250, in order to couple the liquid handling system 250 to a fluid port 222 of the microfluidic cartridge 210. In the orientation of the molecular diagnostic module 130 shown in FIG. 1B, the linear actuator 146 is preferably coupled to the cartridge heater 153 and a portion of the optical subsystem 280, and vertically displaces the cartridge heater 153 and the optical subsystem 280 to position the cartridge heater 153 and the optical subsystem 280 over the microfluidic cartridge 210. The vertical displacement also allows the microfluidic cartridge 210 to receive a magnet 160, which provides a magnetic field to facilitate a subset of a molecular diagnostic protocol, and detection chamber heaters 157, which allows amplification of nucleic acids for molecular diagnostic protocols requiring heating and cooling of the nucleic acid (e.g. PCR). Preferably, the linear actuator 146 is a scissor jack actuator configured to apply substantially uniform pressure over all occlusion positions of a microfluidic cartridge 210 aligned within the molecular diagnostic module 130, and to operate in at least two configurations. In a retracted configuration 146a, as shown in FIG. 4A, the scissor jack actuator has not linearly displaced the cartridge platform 141, and in an extended configuration 146b, as shown in FIG. 4B, the scissor jack actuator has linearly displaced the microfluidic cartridge 210 to position the microfluidic cartridge 210 between the subsystems 153, and 180, and the magnet 160 and detection chamber heaters 157. Additionally, the extended configuration 146b of the scissor jack actuator is configured to couple the nozzle 149 to a fluid port 222 of the microfluidic cartridge 210, such that the liquid handling system 250 can deliver solutions and gases for processing of biological samples. The linear actuator 146 may alternatively be any appropriate linear actuator, such as a hydraulic, pneumatic, or motor-driven linear actuator, configured to linearly displace a microfluidic cartridge within the molecular diagnostic module 130.

As shown in FIGS. 1B, 4A, and 4B, a set of springs 148 is coupled to the cartridge platform 141 and functions to provide a counteracting force against the linear actuator 146 as the linear actuator 146 displaces a microfluidic cartridge 210 resting on the cartridge platform 141. The set of springs 148 thus allows the cartridge platform 141 to return to a position that allows the microfluidic cartridge 210 to be loaded and unloaded from the molecular diagnostic module 130 when the linear actuator 146 is in a retracted configuration 146b, as shown in FIG. 4B. Similarly, the nozzle 149, the heating and cooling subsystem 150, the cartridge heater 153, and the magnet 160 are preferably coupled to springs, such that springs are positioned between elements 149, 150, 153, and 160, and substrates that elements 149, 150, 153, and 160 are mounted to. Alternatively an elastomeric material is preferably positioned between elements 149, 150, 153, and 160, and substrates that elements 149, 150, 153, and 160 are mounted to. The springs and/or elastomeric material function to provide proper functioning and alignment of subsystems of the molecular diagnostic module 130 as the linear actuator 146 is extended or retracted, contributing to reliability and a reduction in stack up tolerance risk. The springs and/or elastomeric material further function to allow more pressure to be applied to occlusion positions of a microfluidic cartridge 210 aligned within the molecular diagnostic module 130, and an appropriate pressure to be applied to elements 149, 150, 153 and 160 of the molecular diagnostic module 130. Thus, proper contact is maintained between elements 149, 150, 153, and 160, and a microfluidic cartridge 210 being manipulated by the molecular diagnostic module. These elements are described in further detail below.

1.1.2 Molecular Diagnostic Module—Heating/Cooling Subsystem and Magnet

The heating and cooling subsystem 150 of the molecular diagnostic module 130 comprises a cartridge heater 153, a fan 155, and a set of detection chamber heaters 157 and functions to controllably heat portions of a microfluidic cartridge 210 for processing of a biological sample containing nucleic acids according to a molecular diagnostic protocol. In the orientation of an embodiment of the molecular diagnostic module 130 shown in FIG. 1B, the cartridge heater 153 is preferably coupled to the linear actuator 146 of the cartridge receiving module 140 and configured to span a central region of a microfluidic cartridge 210 aligned within the molecular diagnostic module 130, the fan 155 is located at a back wall of the cartridge receiving module 140, and the set of detection chamber heaters 157 is located inferior to a set of detection chambers of the microfluidic cartridge 210. In alternative embodiments of the molecular diagnostic module 130, the heating and cooling subsystem 150 can have any appropriate alternative configuration that provides controlled heating and cooling to a microfluidic cartridge within the molecular diagnostic module 130.

The cartridge heater 153, the fan 155, and the set of detection chamber heaters 157 are preferably those described in U.S. application Ser. No. 13/766,359 entitled "System and Method for Processing and Detecting Nucleic Acids" and filed on 13 Feb. 2013, which is incorporated herein in its entirety by this reference; however, in other variations, the cartridge heater 153, the fan 155, and/or the set of detection chamber heaters 157 can be any other suitable cartridge heater 153, fan 155, and/or set of detection chamber heaters 157.

The magnet 160 of the molecular diagnostic module 130 functions to provide a magnetic field for isolation and extraction of nucleic acids bound to magnetic beads within a microfluidic cartridge 210, aligned within the molecular diagnostic module 130. Preferably, the magnet 160 is fixed within the molecular diagnostic module 130, such that the extended configuration 146b of the linear actuator 146 allows the magnet 160 to pass through the magnet receiving slot 144 of the cartridge receiving module 140 and into a magnet housing region 218 of the microfluidic cartridge 210. In an example, the magnet 160 is a rectangular prism-shaped magnet 160 fixed under the cartridge platform 141, and configured to pass through the cartridge platform 141, into a magnet housing region 218 located under the heating region of the microfluidic cartridge 210. Preferably, the magnet 160 is one of two or three magnets lined up in parallel, such that each of the fluidic pathways of a microfluidic cartridge housing the magnets is exposed to two or three times as much magnetic flux, and two to threes times as many opportunities to capture magnetic beads. Alternatively, the magnet 160 is a single magnet configured to expose a set of fluidic pathways to a magnetic field. Preferably, the magnet 160 or group of multiple magnets is coupled to a magnet holder within the molecular diagnostic module 130. Additionally, the magnet holder is preferably composed of an insulating material, such that the magnet holder does not interfere with proper functioning of the cartridge heater 153. Alternatively, the magnet holder may not be composed of an insulating material.

The magnet 160 is preferably a magnet 160 as described in U.S. application Ser. No. 13/766,359 entitled "System and Method for Processing and Detecting Nucleic Acids" and filed on 13 Feb. 2013; however, in other variations, the magnet 160 can be any other suitable magnet. Alternative configurations and/or compositions of the magnet 160 may also be appropriate in facilitating isolation and extraction of nucleic acids bound to magnetic beads within the microfluidic cartridge 210.

1.1.3 Molecular Diagnostic Module—Valve Actuation Subsystem

As shown in FIGS. 5A-5D, the valve actuation subsystem 170 includes an actuation substrate 171 including an array of active regions 172; a set of pins 174, each pin 175 in the set of pins 174 including a base end 176, a distal end 177, and a displacement region 178; a pin housing 180 including a set of cavities 181 that surround and guide displacement of each pin 175 in the set of pins 174; a spring plate 183 including a set of springs 184 coupled to the set of pins 174; and an actuator 187 coupled to at least one of the actuation substrate 171, the pin housing 180, and the spring plate 183, and configured to provide relative displacement between the array of active regions 172 and the set of pins 174. The valve actuation subsystem 170 functions to manipulate a set of occlusion positions of a microfluidic cartridge 210, as described in further detail below, wherein the set of occlusion positions affect sample and/or fluid (e.g., air, reagent, etc.) transfer through fluidic pathways of the microfluidic cartridge 210. As such, the valve actuation subsystem 170 enables portions of the fluidic pathway(s) to be reversibly opened and closed, or maintained in a closed position, by actuation of the set of pins 174. The valve actuation subsystem 170 is preferably situated at a location inferior to that of the cartridge platform 141, as shown in FIG. 1B, such that the set of pins occlude occlusion positions of the microfluidic cartridge 210 in an inferior to superior direction; However, in one alternative variation, the valve actuation subsystem 170 can be situated at a location superior to that of the cartridge platform 141, such that the set of pins occlude occlusion positions of the microfluidic cartridge 210 in a superior to inferior direction. In still other variations, the valve actuation subsystem 170 can be situated relative to the cartridge platform 141 in any other suitable manner.

Figure 5A:
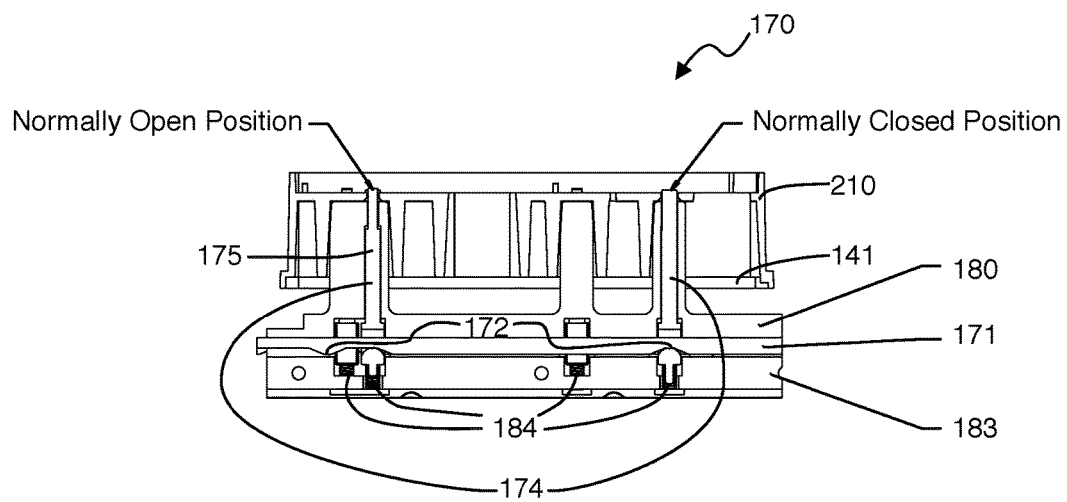
FIGS. 5A-5D depict elements of an embodiment of a valve actuation subsystem of a molecular diagnostic module.
Figure 5B:
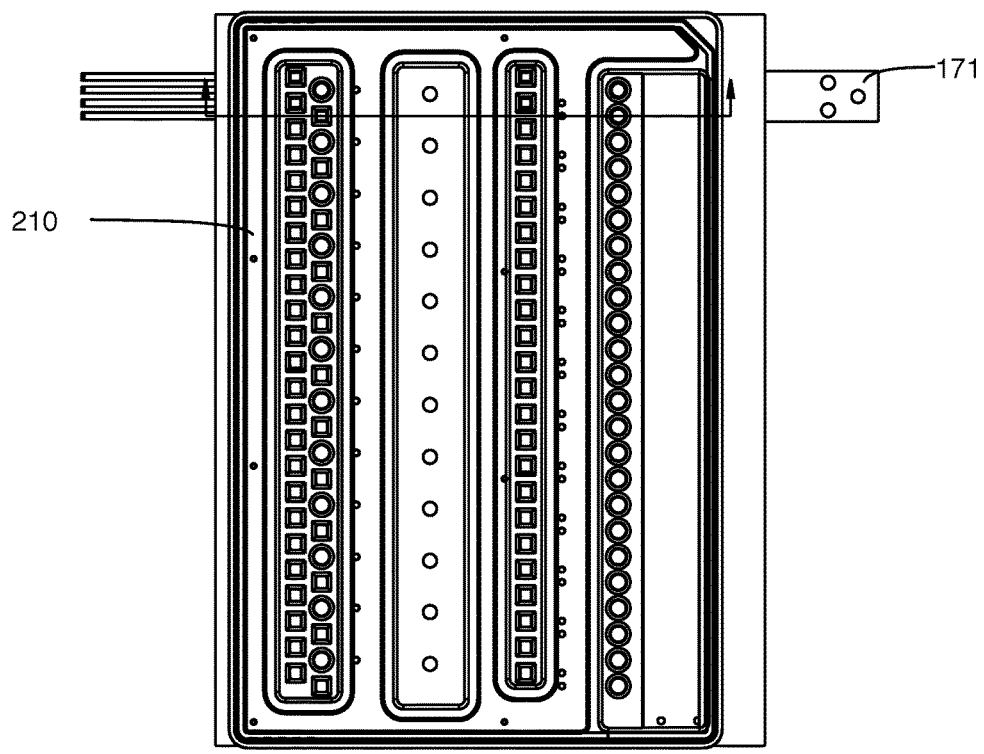
Figure 5C:
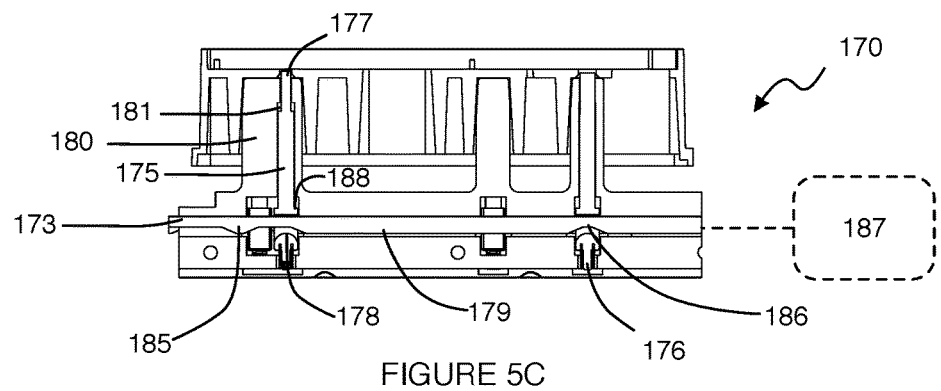
Figure 6A:
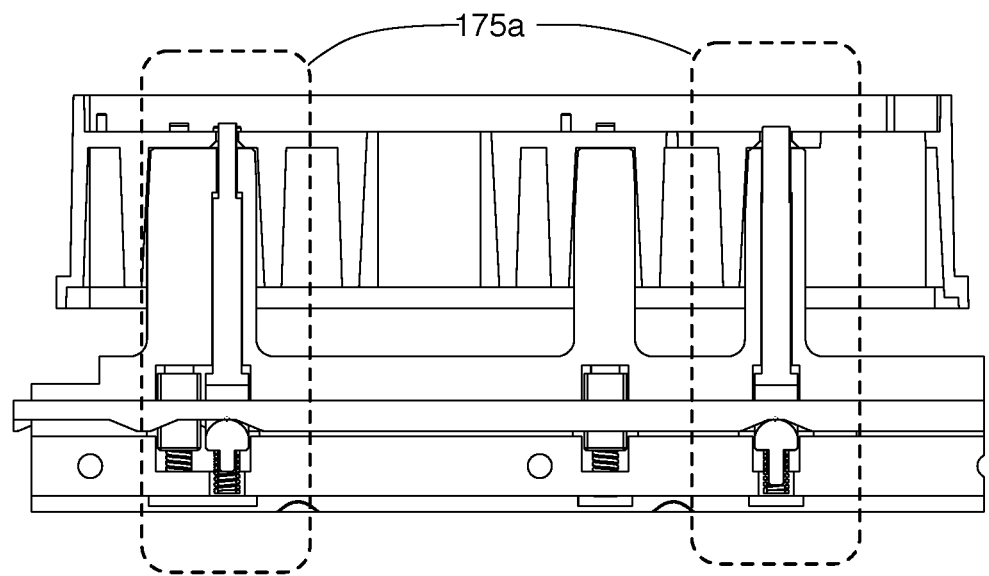
FIGS. 6A-6B depict configurations of an embodiment of a valve actuation subsystem of a molecular diagnostic module.
Figure 6B:
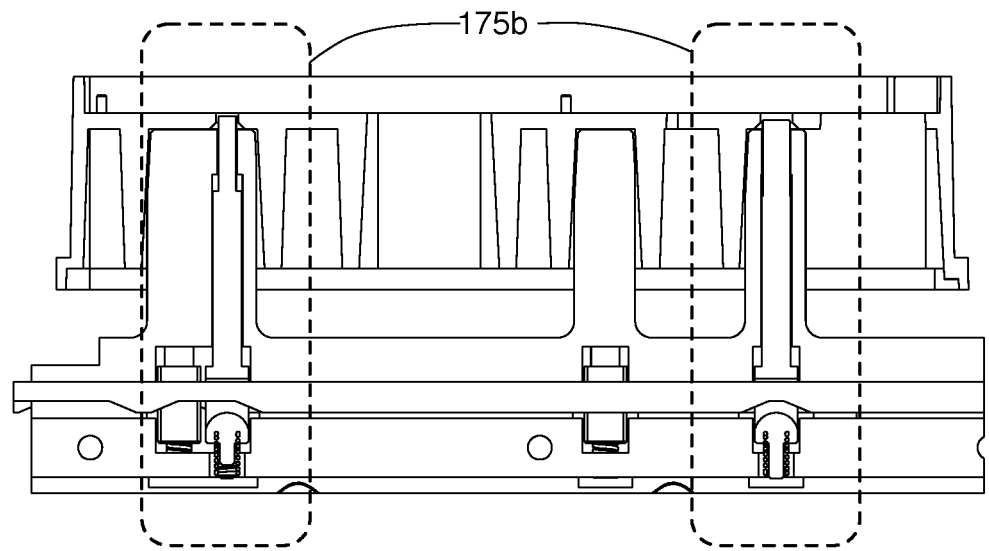

The actuation substrate 171 includes an array of active regions 172, which function to interact with one or more displacement regions 178 of the set of pins 174, in order to transition pins 175 of the set of pins 174 into extended configurations 175*a* and/or retracted configurations 175*b*, as shown in FIGS. 6A and 6B. The array of active regions 172 is preferably configured such that subsets of the set of pins 174 can be placed into specific and repeatable configurations (e.g., an array of extended and retracted configurations), in order to manipulate fluidic pathways of the microfluidic cartridge 210 in a repeatable manner for processing nucleic acids. Preferably, the actuation substrate 171 transforms lateral motion of the actuation substrate 171 into vertical actuation of one or more pins of the set of pins 174, in the orientation shown in FIGS. 5A and 5C; however, in other variations, the valve actuation subsystem 171 can be configured to transform any other suitable motion (e.g., rotational motion, non-lateral motion, etc.) of the actuation substrate 171 into actuation of one or more pins of the set of pins 174.

The array of active regions 172 preferably includes elements that physically contact the set of pins 174 during motion of the actuation substrate 171, thereby directly moving one or more pins 175 of the set of pins 174 into a desired configuration. In one such variation, the array of active regions 172 includes at least one protrusion (e.g., peak) and can additionally or alternatively include at least one recessed area (e.g., valley) that physically enable raising and/or lowering of the pin(s) of the set of pins 174. In one alternative, the array of active regions 172 can include elements that transmit forces to the pin(s) of the set of pins 174, thereby moving the pin(s) into a desired configuration without physical contact. In one such variation, the array of active regions 172 includes an array of magnetic elements that produce magnetic fields that enable raising and/or lowering of the pin(s) of the set of pins 174. In any of these variations, elements of the array of active regions 172 can be situated at a first surface 179 of the actuation substrate 171, such that motion of the actuation substrate 171 is transformed into actuation of pins contacting the first surface 179 of the actuation substrate. The first surface 179 can be an inferior surface of the actuation substrate 171, in the orientation shown in FIGS. 5A and 5C, or a superior surface of the actuation substrate 171. In other variations, however, the elements of the array of active regions 172 can be situated at multiple surfaces of the actuation substrate 171, and can additionally or alternatively be embedded within the actuation substrate 171 (e.g., as in an embedded array of magnetic elements). Furthermore, the actuation substrate 171 can include combinations of elements that physically contact the set of pins 174 and elements that transmit forces to the set of pins 174 without physical contact.

In a first variation, as shown in FIG. 5C, the actuation substrate 171 comprises a cam card 173 including a set of peaks 185 and valleys 186, and functions to transform linear motion in one plane to vertical motion in another plane. In the first variation, the cam card 173 contacts the displacement regions 178 of pins in a set of pins 172, such that when a peak 185 of the cam card 173 enters alignment with a displacement region 178, the pin is in one configuration, and when a valley 186 of the cam card 173 enters alignment with a displacement region, the pin is in a another configuration. Every peak in the set of peaks 185 and valleys 186 is preferably identical in morphology and dimension; however, in variations, the set of peaks 185 and valleys 186 can include one or more peaks having different dimensions and/or morphologies from other peaks in the set of peaks 185 and valleys 186. Similarly, every valley in the set of peaks 185 and valleys 186 is preferably identical in morphology and dimension; however, in variations, the set of peaks 185 and valleys 186 can include one or more valleys having different dimensions and/or morphologies from other valleys in the set of peaks 185 and valleys 186. As such, the set of peaks 185 and valleys 186 can be configured to provide an identical range of motion for every pin 175 in the set of pins 174, or can be configured to provide different ranges of motion for pins of the set of pins 175. In still other variations, peaks and/or valleys of the set of peaks 185 and valleys 186 can be adjustable in dimension in order to provide adjustable ranges of motion or to compensate for wear of peaks and/or valleys.

In the first variation of the actuation substrate 171, the peaks 185 and valleys 186 of the cam card 173 are preferably in a set configuration, as shown in FIG. 5C, such that lateral motion of the cam card 173 to a set position places the set of pins 174 in a specific configuration in a reversible and/or repeatable manner. The set configuration further functions to enable manipulation of normally closed and normally open occlusion positions, in a specific configuration, of a microfluidic cartridge 210 interacting with the valve actuation subsystem 170. As such, lateral movement of the cam card 173 to different positions of a set of positions consistently places subsets of the set of pins 172 into desired configurations to occlude different portions of a fluidic pathway of a microfluidic cartridge 210 in contact with the set of pins 174. Thus, desired portions of a fluidic pathway of the microfluidic cartridge 210 can be selectively occluded and opened to facilitate processing of a biological sample according to any appropriate tissue, cellular, or molecular diagnostic assay protocol.

In the first variation of the actuation substrate 171, the set of peaks 185 and valleys 186 of the cam card 173 are situated at a first face 179 of the cam card 173, such that lateral motion of the cam card 173 is transformed into actuation of pins contacting the first face 179 of the cam card 173. In the first variation, the first face 179 is oriented away from distal ends 177 of the set of pins 174, as described in further detail below, such that peaks 185 of the cam card 173 are configured to retract pins of the set of pins 174, and valleys of the cam card 173 are configured to enable extension of pins of the set of pins. In another variation, however, the set of peaks 185 and valleys 186 can be situated at multiple faces of the cam card 173.

In the first variation, the cam card 173 is configured to be laterally displaced in one coordinate direction within a plane (e.g., by a linear actuator); however in another variation, the cam card 173 is configured to be laterally displaced in only multiple directions within a plane (e.g., by multiple linear actuators, by an x-y linear actuator). In a specific example, the peaks 185 of the cam card 173 are raised 1 mm above the valleys 186 of the cam card 173. In the specific example, the peaks 185 are identical and have a substantially semicircular cross section with a radius of 1 millimeter, while the valleys 186 are substantially planar and situated in line with the base of each peak 185. Alternative variations can, however, include any appropriate configurations and geometries of a cam card 173 with peaks 185 and valleys 186, driven by any appropriate actuator.

In alternative embodiments of the actuation substrate 171, the actuation substrate 171 can be a cam wheel comprising an array of active regions 172 configured to enable actuation of pins contacting a cylindrical surface, and configured to convert rotary motion to linear (i.e., vertical) motion of the set of pins 174. The cam wheel can be configured to contact base ends 176 of pins in the set of pins 174, and can be coupled to a motor shaft and driven by a motor. In other alternative embodiments of the actuation substrate 171, the actuation substrate 171 can altogether be replaced by a set of cams, each configured to individually rotate about an axis. In these alternative embodiments, rotating subsets of the set of cams raises/lowers corresponding subsets of the set of pins 174, and occludes specific portions of a of a microfluidic cartridge 210 in contact with the set of pins 174.

The set of pins 174 is configured to interact with the actuation substrate 171, and functions to enable selective occlusion and/or opening of fluidic pathways of the microfluidic cartridge 210, by way of the set of occlusion positions. The pins of the set of pins 174 preferably include cylindrical portions and, in the orientation shown in FIGS. 5A and 5C, each pin in the set of pins 174 preferably has a portion defining a circular cross section configured to facilitate sliding within a pin housing 180. Alternatively, each pin can comprise any appropriate cross-sectional geometry (e.g., rectangular) and/or end shape (e.g., flat or pointed) to facilitate occlusion of a fluidic pathway of a microfluidic cartridge 210. Preferably, the surface of each pin in the set of pins 174 is composed of a low-friction material to facilitate sliding motions (i.e., in cooperation with an actuation substrate 171 or within a pin housing 180); however, each pin may alternatively be coated with a lubricant configured to facilitate sliding motions. In a specific example, the valve actuation subsystem 170 comprises 12 sets of pins 174 configured to selectively occlude 12 fluidic pathways of a microfluidic cartridge 210 aligned within the molecular diagnostic module 130; however, other embodiments can comprise any other suitable number of sets of pins 174.

Each pin 175 in the set of pins 174 preferably includes a base end 176, a distal end 177, and a displacement region 178. As shown in FIG. 5C, one or more pins 175 of the set of pins 174 can additionally include a stop region 188 configured to interface with the pin housing 180 in a manner that defines a range of motion for the pin(s) including a stop region 188. The base end 176 of a pin 175 functions to interact with springs of a spring plate 183, wherein the springs 184 provide a biasing force against pins of the set of pins 174, as described in further detail below. As such, the base end 176 can be configured to abut a spring of the spring plate 183, and can additionally or alternatively be coupled to the spring of the spring plate 183 in any other suitable manner. The distal end 177 of a pin 175 functions to interact with an occlusion position of a fluidic pathway of a microfluidic cartridge 210 aligned with the valve actuation subsystem 170 of an embodiment of the molecular diagnostic module 130. The base end 176 and/or the distal end 177 of a pin 175 can be cylindrical in morphology, in order to provide an occlusion surface that is substantially circular, ovaloid, or ellipsoidal. However, in some variations, the base end 176 and/or the distal end 177 of pin 175 can be polygonal prismatic (e.g., square prismatic, triangular prismatic) in order to provide an occlusion surface that is polygonal, or amorphous prismatic in morphology. Furthermore, in alternative variations, any suitable portion of a pin 175 can be configured to interact with a spring in order to provide a biasing force against the pin 175.

The displacement region 178 of a pin 175 functions to interact with one or more active regions of the array of active regions to enable actuation of the pin 175. Preferably, the displacement region 178 is substantially aligned with the actuation substrate 171, in order to facilitate interaction between an active region 172 of the actuation substrate 171 and a displacement region 178 of a pin 175. Additionally, the displacement region 178 preferably mechanistically complements one or more active regions 172 of actuation substrate 171. As such, the displacement region can include a portion that physically contact an active region 172 during motion of the actuation substrate 171, and in one such variation, the displacement region 178 includes at least one protrusion (e.g., peak) or recessed area (e.g., valley) that physically interacts with the active region to raise or lower the pin 175. In one alternative, the displacement region 178 can include additionally or alternatively include a portion that responds to forces provided by the active region(s) 172 of the actuation substrate 171, thereby moving the pin into a desired configuration without physical contact between the pin 175 and an active region. In one such variation, the displacement region can include a magnetic element that responds to magnetic fields produced by active regions of the actuation substrate 171 to raise or lowering the pin. In this variation, the magnetic element of the displacement region 178 can be configured to be drawn toward the magnetic element of an active region 172, or can be configured to be repelled away from the magnetic element of the active region 172.

Figure 7A:
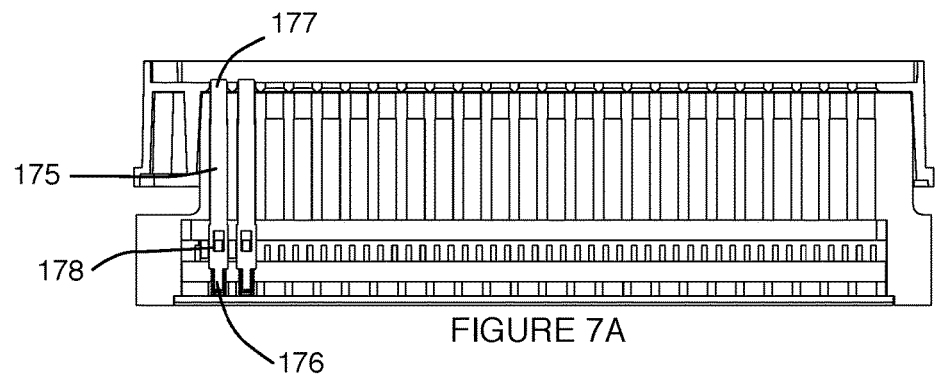
FIGS. 7A-7C depict elements of an embodiment of a valve actuation subsystem of a molecular diagnostic module.
Figure 7B:
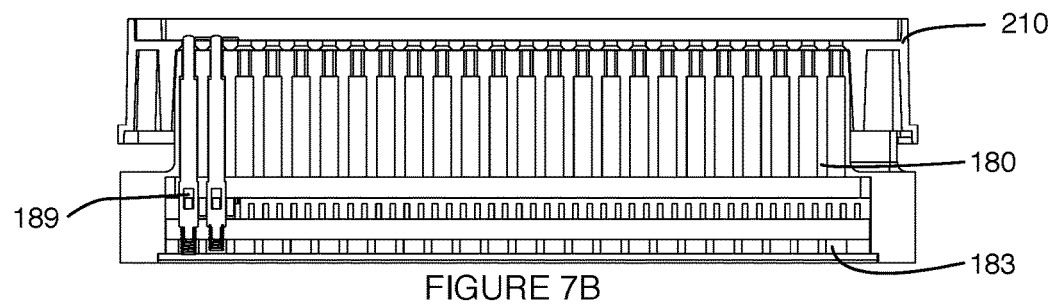
Figure 7C:
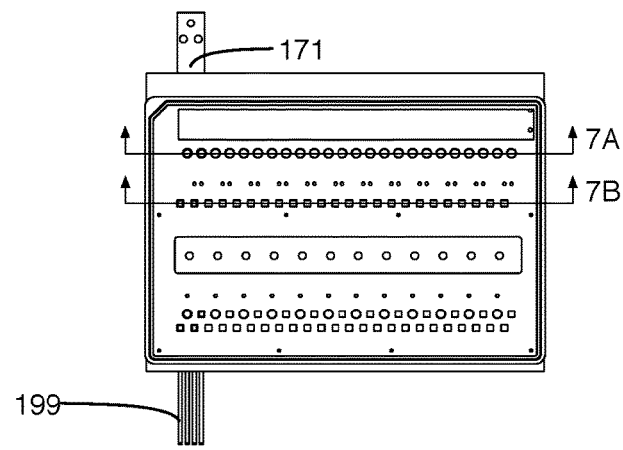
Figure 8A:
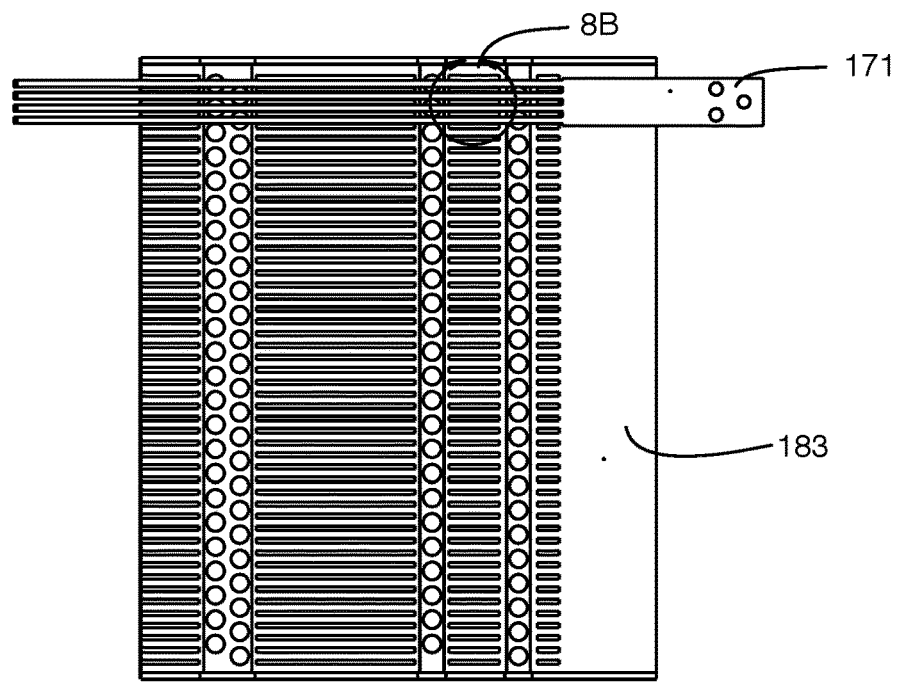
FIGS. 8A and 8B depict elements of an example of a valve actuation subsystem of a molecular diagnostic module.
Figure 8B:
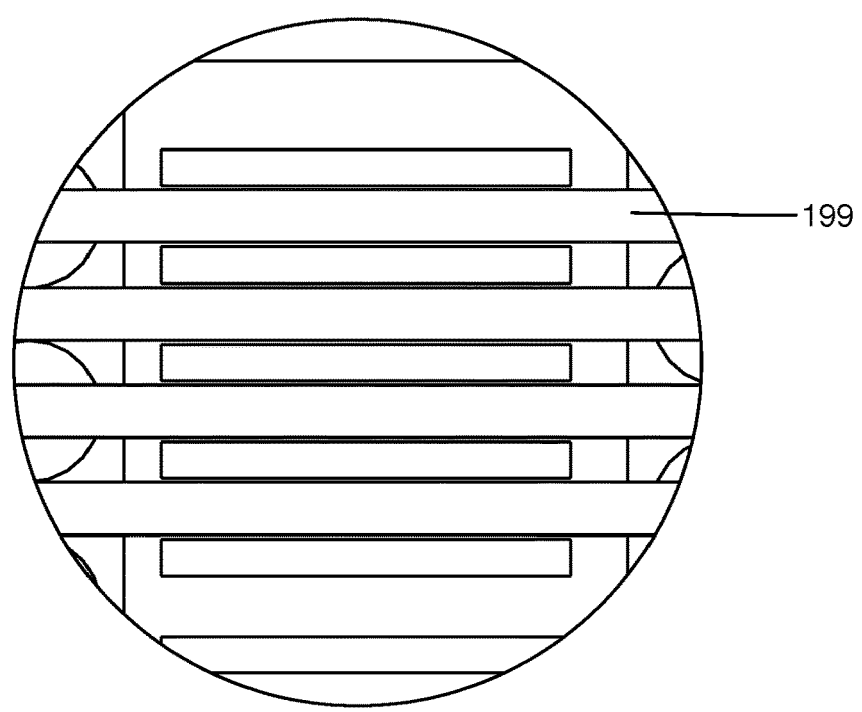

As shown in FIGS. 7A-7C, the displacement region 178 of a pin 175 is preferably incorporated within the body of the pin 175, between the base end 176 and the distal end 177 of the pin 175. In one variation, the displacement region 178 can be incorporated within an opening 189 defined within the body of the pin 175. However, the displacement region 178 of a pin 175 can additionally or alternatively be biased toward an exterior surface of the pin 175, defined at least in part at a recessed region of the exterior surface of the pin 175, or coupled to the pin in any other suitable manner (e.g., using an extension configured to transmit motion from the displacement region to the pin).

In a first specific example, the displacement region 178 includes a semi-cylindrical protrusion defined within a slotted opening 189, wherein the base of the semi-cylindrical protrusion is situated at the base end of the slotted opening (i.e., toward the base end 176 of the pin 175). In the first specific example, the actuation substrate 171 thus comprises at least one arm 199 including an active region 172 (e.g., a peak, a valley), as shown in FIG. 7C, wherein the arm 199 is configured to pass through the slotted opening 189 of the pin 175, and wherein movement of the arm 199 to place the active region 172 into alignment with the protrusion (i.e., the displacement region 178) results in actuation of the pin 175. In a variation of the first specific example, a magnetic element proximal a surface of the slotted opening of the displacement region 178 of the pin 175 can be configured to interact with a corresponding magnetic element (i.e., an active region 172) of an arm 199 of the actuation substrate 171. In this variation, the magnetic element of the arm 199 can be configured to magnetically repel or draw the magnetic element of the displacement region 178 of the pin 175, in order to provide actuation of the pin. In other examples, however, the displacement region 178 of a pin can be configured to complement configurations of active regions 172 of the actuation substrate 171 in any other suitable manner.

The stop region 188 is preferably a protruding portion of a pin 175 that interacts with a complementary portion of the pin housing 180, such that the complementary portion of the pin housing obstructs further motion of the pin 175. The stop region 188 can comprise a region of the pin 175 that has a larger width or diameter than other regions of the pin 175, and can additionally or alternatively include a protrusion that limits range of motion of the pin in any other suitable manner. In an example shown in FIG. 5C, a pin 175 includes a stop region 188 located between the base end 176 and the distal end 177 of a pin 175 and defined by a larger diameter than that of the pin housing 180. In other variations of the specific example, however, the stop region 188 of the pin 175 can be located at any other suitable position along the length of the pin 175. Furthermore, each pin 175 of the set of pins 174 can include multiple stop regions 188 configured to define ranges of motion for the set of pins.

Each pin 175 in the set of pins 174 preferably operates in an extended configuration 175*a* and/or a retracted configuration 175*b*. Preferably, each pin 175 of the set of pins 174 is configured to reversibly and repeatably transition between the extended configuration 175*a* and the retracted configuration 175*b*. However, in alternative variations, one or more pins 175 of the set of pins 174 can be configured to achieve only one of the extended configuration 175*a* and the retracted configuration 175*b*, and/or a pin 175 of the set of pins 174 can be configured to be locked semi-permanently in a configuration 175*a*, 175*b* upon entering the configuration 188, 189. In the extended configuration 175*a*, the distal end 177 of the pin 175 is configured to protrude from an opening of the pin housing 180, in order to provide an occluding force at a fluidic pathway of a microfluidic cartridge 210 interacting with the valve actuation subsystem 170. In the retracted configuration 175*b*, the distal end 177 of the pin 175 is configured to retract from the opening of the pin housing 180, in order to remove an occluding force at a fluidic pathway of a microfluidic cartridge 210 interacting with the valve actuation subsystem 170. Preferably, in relation to variations described above, the extended configuration is activated by translation of the active region (e.g., a peak, a magnet) away from the displacement region, and the retracted configuration is activated by translation of an active region (e.g., a peak, a magnet) of the actuation substrate into alignment with the displacement region. As such, in an example with the orientation shown in FIGS. 6A and 6B, the extended configuration 175*a* is activated as a peak of the actuation substrate 171 is moved away from the protrusion of the displacement region 178 of a pin 175, and the retracted configuration 175*b* is activated as a peak of the actuation substrate 171 is moved into alignment with the protrusion of the displacement region 178 (i.e., the peak of the actuation substrate 171 pushes the pin 175 downward by way of the protrusion in the displacement region 178). The extended and retracted configurations 175*a*, 175*b* can, however, be activated in any other suitable manner.

The pin housing 180 includes a set of cavities 181, which function to surround and guide displacement of each pin 175 in the set of pins 174. As such, the pin housing 180 functions to constrain and guide motion of each pin 175 in the set of pins 174, as the actuation substrate 171 moves and interacts with the set of pins 174. In one variation, each pin 175 in the set of pins 174 is surrounded by an individual cavity of the set of cavities 181; however, in another variation a cavity of the set of cavities 181 can be configured to surround multiple pins in the set of pins 174. In an example shown in FIGS. 5A-5D, the pin housing 180 is located under the cartridge platform 141, such that the set of cavities 181 is aligned with the set of access regions 145, to provide access, by the set of pins 174, to a microfluidic cartridge 210 aligned on the cartridge platform 141. In the example, the pin housing 180 thus constrains the set of pins 174, such that each pin can only move linearly in a vertical direction, and with a set range of motion. Each cavity of the set of cavities 181 preferably has a constricted region (i.e., serving as a pin stop) configured to limit the motion of a pin within a cavity (i.e., by way of the stop region 188 of the pin); however, each cavity of the set of cavities 181 may alternatively not include a constricted region. Preferably, surfaces of the pin housing 180 contacting the set of pins 174 are composed of a low friction material to facilitate sliding of a pin 175 within a cavity of the pin housing 180; however, surfaces of the pin housing 180 contacting the set of pins 174 may alternatively be coated with a lubricant configured to facilitate sliding motions. Other variations of the pin housing 180 and the set of pins 174 may include no additional provisions to facilitate sliding of a pin 175 within a cavity of the set of cavities 181.

The spring plate 183 includes a set of springs 184 coupled to the set of pins 174, and functions to provide biasing forces against the set of pins, in order to bias each pin in the set of pins in a specific direction. The spring plate 183 is preferably situated proximal the base ends 176 of the set of pins 174; however, the spring plate 183 can alternatively be configured relative to other elements of the valve actuation subsystem 170 in any other suitable manner. A spring of the set of springs 184 preferably functions to provide a counteracting force to restore a pin to a desired configuration (e.g., an extended configuration 175*a*, a retracted configuration 175*b*). Furthermore, a spring of the set of springs 184 can additionally function to allow sufficient force to be transmitted through the pin 175 to fully occlude a microfluidic channel of a microfluidic cartridge 210, while preventing forces from being generated that could damage the pin 175, the microfluidic cartridge 210, and/or the actuation substrate 171. Preferably, a spring of the set of springs 184 is configured to abut the base end 176 of a pin 175, and/or a region substantially proximal the base end 176 of the pin 175 in order to transmit a biasing force to the pin 175. However, a spring of the set of springs 184 can additionally or alternatively be configured to couple to any other suitable portion of a pin 175. Furthermore, the set of springs 184 can be configured to bias every pin of the set of pins 174 in the same direction with identical magnitudes of force; however, in other variations, the set of springs 185 can be configured to bias different pins of the set of pins 175 in different directions, and/or with different magnitudes of force.

In a first variation, the set of springs 184 is configured to bias every pin 175 of the set of pins 174 toward an extended configuration 175a, such that when an active region (e.g., a peak, a magnet) of the actuation substrate 171 substantially enters alignment with a displacement region 178 of a pin 175, the pin 175 is transitioned into a retracted configuration 175b and the spring contacting the pin is compressed (e.g., further compressed, transitioned from a neutral state to a state of compression). Then, in the first variation, when the active region of the actuation substrate 171 is moved out of alignment with the displacement region 178, the pin 175 is restored to an extended state. In other variations, however, the spring(s) of the set of springs 184 can be configured to bias the pin(s) of the set of pins 174 toward a retracted configuration 175b, such that alignment of the active region(s) of the actuation substrate 171 with the displacement region(s) 178 of the pin(s) transitions the pin(s) into an extended configuration 175a. In still other variations, the springs can be configured to bias the pins in any other suitable manner.

Figure 5D:
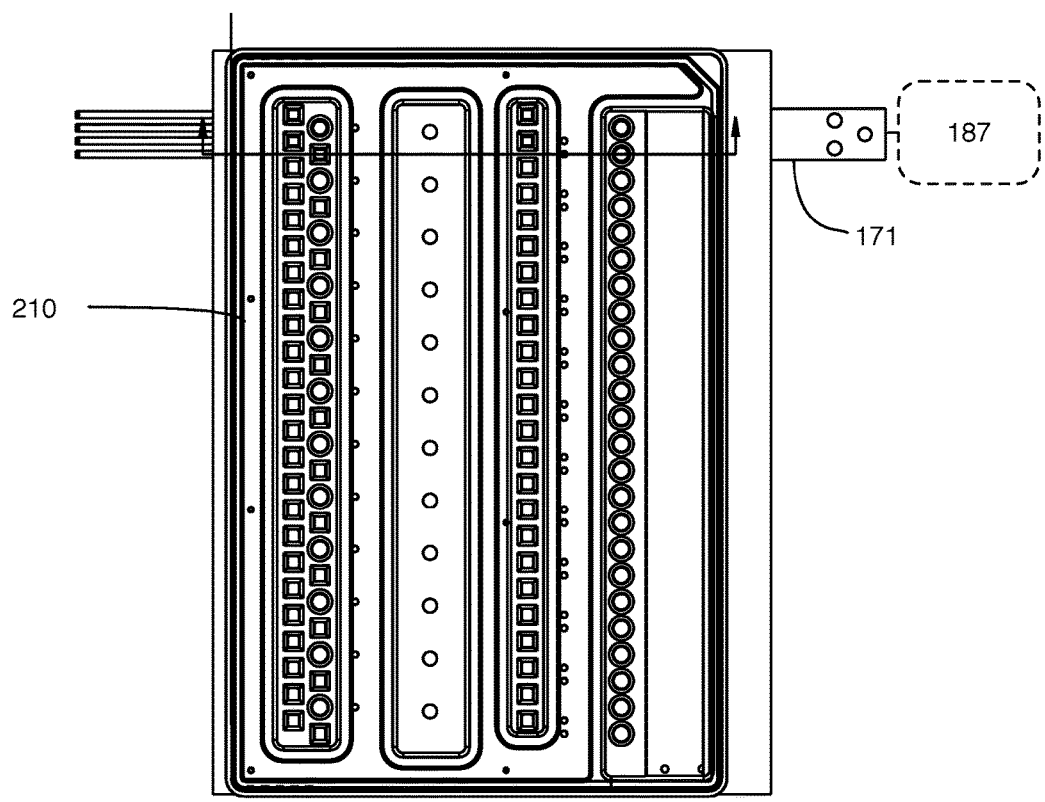

The actuator 187 is coupled to at least one of the actuation substrate 171, the pin housing 180, and the spring plate 183, and functions to provide relative displacement between the array of active regions 172 and the set of pins 174, thus transforming motion of the actuation substrate 171 into motion of subsets of the set of pins 174. The actuator 187 is preferably a linear actuator; however, the actuator 187 can additionally or alternatively comprise any other suitable actuator. Preferably, the actuator 187 is coupled to the actuation substrate 171 with the set of pins 174, the spring housing 180, and the spring plate 183 substantially stationary, such that actuation of the actuator 187 manipulates motion of the set of pins 174 in order to occlude pathways of the microfluidic cartridge 210. In one such variation, as shown in FIGS. 5C and 5D, the actuator can be coupled to one end of the actuation substrate 171 (e.g., using a set of coupling points defined within the actuation substrate 171); however, in other variations, the actuator 187 can be coupled to any other suitable portion of the actuation substrate 171. Alternatively, the actuator 187 can be configured to move the set of pins 174, within the pin housing 180, relative to the actuation substrate 171, in order to occlude pathways of the microfluidic cartridge 210. In still other variations, the actuator 187 can be coupled to any other suitable portion of the valve actuation subsystem 170.

In one specific example of the valve actuation subsystem 170 shown in FIGS. 5A-5D, 7A-7C, and 8A-8B, the set of pins 174 and the pin housing 180 are located directly under the microfluidic cartridge 210, after the microfluidic cartridge 210 has been aligned within the molecular diagnostic module 130, such that the set of pins can access the microfluidic cartridge 210 through the access regions 145 of the cartridge platform 141. The actuation substrate 171 in the specific example is situated amongst the set of pins 174, between base ends and distal ends of the set of pins 174, and comprises a set of arms including the active regions 172 (i.e., peaks and valleys) defined at a bottom face of the arms 199 of the actuation substrate, in the orientation shown in FIG. 5C. In the specific example, peaks 185 of the actuation substrate 171 are configured to push pins downward to a retracted configuration 189 by way of semi-cylindrical protrusions defined within slotted openings 189 of the pins 175, and valleys 186 of the actuation substrate 171 are configured to restore pins 175 of an extended configuration 188. In the specific example, The actuation substrate 171 includes four parallel arms 199 configured to manipulate eight occlusion positions of a microfluidic cartridge 210, with each arm 199 configured to pass through slotted openings in two pins 175, in order to manipulate two occlusion positions of the microfluidic cartridge 210. The four parallel arms 199 include a first arm including two peaks and two valleys, in alternation, configured to manipulate two normally open occlusion positions, a second arm including two valleys, configured to manipulate two normally closed occlusion positions, a third arm including two peaks and two valleys, in alternation, configured to manipulate two normally open occlusion positions, and a fourth arm including a peak and two valleys, configured to manipulate one normally open occlusion position and one normally closed occlusion position. Normally open and normally closed occlusion positions are further described in U.S. application Ser. No. 13/765,996 filed on 13 Feb. 2013 and entitled "Microfluidic Cartridge for Processing and Detecting Nucleic Acids", which is incorporated herein in its entirety by this reference. In the specific example, each arm has a width of ~1.22 millimeters, and is spaced apart from other arms by a gap of ~1 millimeter. The actuation substrate 171 in the specific example further has a maximum width of ~8.74 millimeters and a length of 13.74 centimeters, with peaks having heights 1 millimeter and valleys having depths of 1 millimeter.

In the specific example, the actuation substrate 171 is coupled to an actuator 187 at an end opposite the arms 199 of the actuation substrate 171, by way of three coupling points, as shown in FIG. 5D. The actuator 187 is configured to laterally displace the actuation substrate 171 to vertically displace one or more pins 175 of the set of pins 174. The actuation substrate in the specific example travels on a low friction surface configured to facilitate lateral displacement of the actuation substrate 171; however, in other variations, the actuation substrate 171 can additionally or alternatively be configured to travel through any other suitable environment having low friction (e.g., air, lubricated surface, surface of ball bearings, etc.) in order to facilitate actuation of the actuation substrate 171.

While the system 100 preferably includes an embodiment, variation, or specific example of the valve actuation subsystem 170 described above, the system can alternatively or additionally include any other suitable valve actuation subsystem 170, such as a valve actuation subsystem described in U.S. application Ser. No. 13/766,359 entitled "System and Method for Processing and Detecting Nucleic Acids" and filed on 13 Feb. 2013.

1.1.4 Molecular Diagnostic Module—Optical Subsystem

As shown in FIGS. 1B and 8, the optical subsystem 280 of the molecular diagnostic module 130 comprises a set of light emitting elements 281, a set of excitation filters 282 configured to transmit light from the set of light emitting elements 281, a set of dichroic mirrors 283 configured to reflect light from the set of excitation filters 282 toward a set of apertures 285 configured to transmit light toward a set of nucleic acid samples, a set of emission filters 286 configured to receive and transmit light emitted by the set of nucleic acid samples, and a set of photodetectors 287 configured to facilitate analysis of light received through the set of emission filters 286. The optical subsystem 280 can further comprise a set of lenses 284 configured to focus light onto the set of nucleic acid samples. The optical subsystem 280 thus functions to transmit light at excitation wavelengths toward a set of nucleic acid samples and to receive light at emission wavelengths from a set of nucleic acid samples. Preferably, the optical subsystem 280 is coupled to an optical subsystem actuator 288 configured to laterally displace and align the optical subsystem 280 relative to the set of nucleic acid samples, and is further coupled to a linear actuator 146 of the cartridge receiving module 140 to position the optical subsystem 280 closer to the set of nucleic acid samples. Alternatively, the optical subsystem 280 may not be coupled to a linear actuator 146 of the cartridge receiving module 140, and may only be configured to translate laterally in one direction. In a specific example, the optical subsystem 280 is located within the molecular diagnostic module 130 and coupled to the linear actuator 146 of the cartridge receiving module 140, such that, in the extended configuration 146b of the linear actuator 146, the optical subsystem 280 can be positioned closer to a microfluidic cartridge 210 aligned within the molecular diagnostic module. Conversely in the specific example, the optical subsystem 280 is positioned away from the microfluidic cartridge 210 in the retracted configuration 146a of the linear actuator 146. In the specific example, the optical subsystem 280 is further coupled to an optical subsystem actuator 288 configured to laterally displace the optical subsystem 280 relative to the microfluidic cartridge 210, such that the optical subsystem 280 can be aligned with a set of detection chambers of the microfluidic cartridge 210.

The optical subsystem 280 is preferably an optical subsystem 280 as described in U.S. application Ser. No. 13/766,359 entitled "System and Method for Processing and Detecting Nucleic Acids" and filed on 13 Feb. 2013; however, in other variations, the optical subsystem 180 can additionally or alternatively include any other suitable optical subsystem elements configured to transmit excitation wavelengths of light to samples, and/or receive emission wavelengths of light from the samples.

1.2 System—Microfluidic Cartridge

Figure 9:
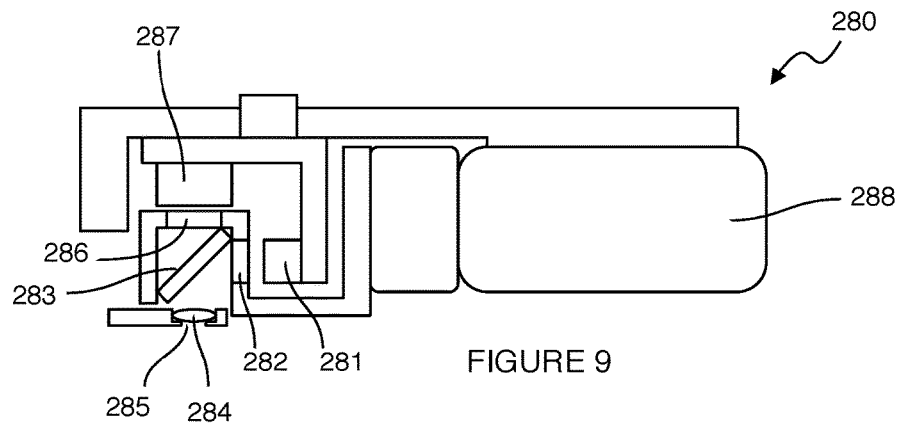
FIG. 9 depicts elements of an embodiment of an optical subsystem of a molecular diagnostic module.

The microfluidic cartridge 210 functions to receive a set of magnetic bead-samples, facilitate separation of nucleic acids from the set of magnetic bead-samples, receive a set of nucleic acid-reagent samples, and facilitate analysis of nucleic acids from the set of nucleic acid-reagent samples. In one embodiment, as shown in FIGS. 9A and 9B, the microfluidic cartridge 210 comprises a top layer 211 including a set of sample port-reagent port pairs 212 and a set of detection chambers 213; an intermediate substrate 214, coupled to the top layer 211 and partially separated from the top layer 211 by a film layer 215, configured to form a waste chamber 216; an elastomeric layer 217 partially situated on the intermediate substrate 214; a magnet housing region 218 accessible by a magnet 160 providing a magnetic field; and a set of fluidic pathways 219, each formed by at least a portion of the top layer 211, a portion of the film layer 215, and a portion of the elastomeric layer 217. In the embodiment, the microfluidic cartridge 10 further comprises a bottom layer 221 coupled to the intermediate substrate 214 and configured to seal the waste chamber 216. Furthermore, in the embodiment, the top layer 211 of the microfluidic cartridge 210 further comprises a shared fluid port 222, a vent region 223, and a heating region 224, such that each fluidic pathway 220 in the set of fluidic pathways 219 is fluidically coupled to a sample port-reagent port pair 229, the shared fluid port 222, the waste chamber 216, and a detection chamber 225, comprises a turnabout portion configured to pass through the heating region 224 and the magnetic field, and is configured to pass through the vent region 223 upstream of the detection chamber 225. Each fluidic pathway 220 thus functions to receive and facilitate processing of a sample fluid containing nucleic acids as it passes through different portions of the fluidic pathway 220.

The microfluidic cartridge 210 is preferably configured to be received and manipulated by the molecular diagnostic module 130, such that the cartridge receiving module 140 of the molecular diagnostic module 130 receives and aligns the microfluidic cartridge 210 within the molecular diagnostic module 130, the heating and cooling subsystem 150 of the molecular diagnostic module 130 is configured to transfer heat to the heating region 224 of the microfluidic cartridge 210, and the magnet 160 of the molecular diagnostic module 130 is configured to be received by the magnet housing region 218 of the microfluidic cartridge 210 to provide a magnetic field for separation of nucleic acids. Additionally, the shared fluid port 222 of the microfluidic cartridge 210 is configured to couple to a nozzle 149 coupled to the linear actuator 146 of the cartridge receiving module 140, such that the liquid handling system 250 can deliver fluids and gases through the shared fluid port 222. The elastomeric layer 217 of the microfluidic cartridge 210 is also preferably configured to be occluded at a set of occlusion positions 226 by the valve actuation subsystem 170 of the molecular diagnostic module, in order to occlude portions of a fluidic pathway 220 of the microfluidic cartridge 210 for processing of a set of biological samples. The optical subsystem 180 of the molecular diagnostic module 130 is further configured to align with the set of detection chambers 213 of the microfluidic cartridge 210, to facilitate analysis of a set of nucleic acid samples. The microfluidic cartridge 210 is preferably the microfluidic cartridge 210 described in U.S. application Ser. No. 13/765,996 and filed on 13 Feb. 2013, which is incorporated in its entirety by this reference, but can alternatively be any appropriate cartridge or substrate configured to receive and process a set of samples containing nucleic acids.

1.3 System—Liquid Handling System

Figure 10A:
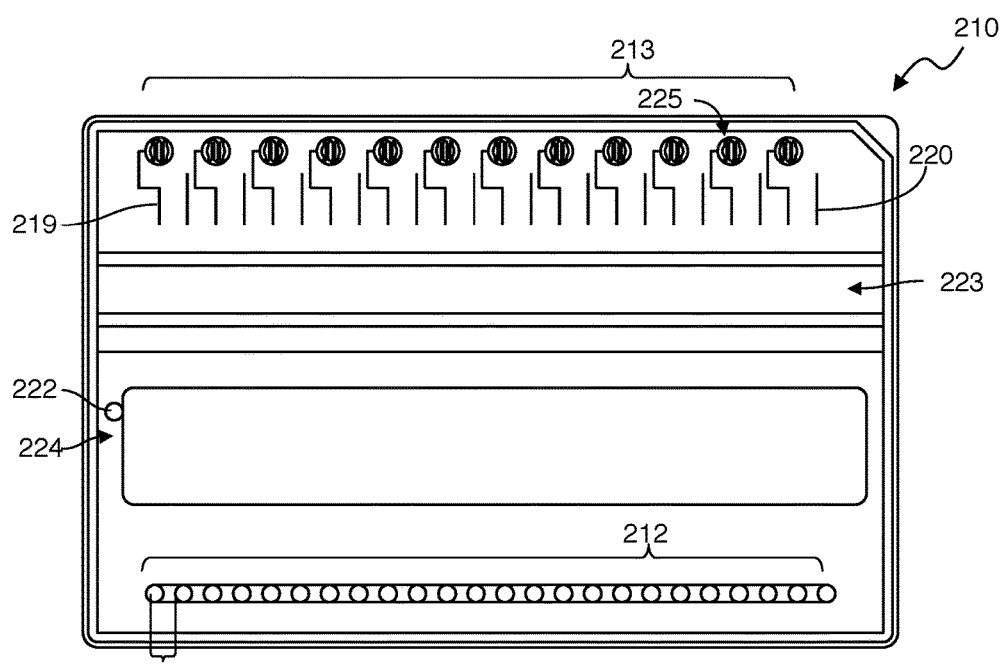
FIGS. 10A-10B depict an embodiment of a microfluidic cartridge for processing biological samples.
Figure 10B:
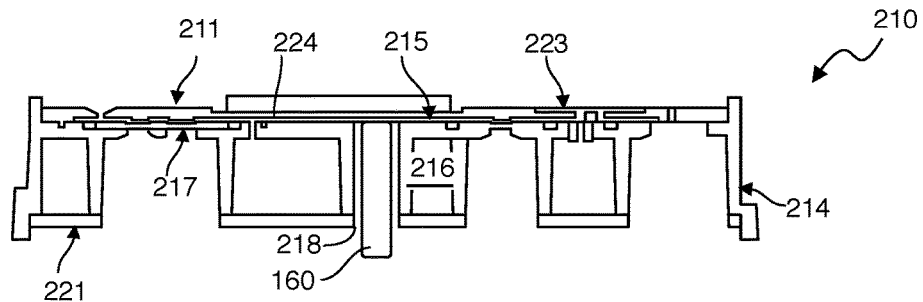

The liquid handling system 250 of the system 100 includes a liquid handling arm 255 and a syringe pump 265, as shown in FIGS. 10A-10C and functions to deliver biological samples, reagents, and gases to elements of the system 100. As described in Section 1, an embodiment of the liquid handling system 250 is configured to aspirate a set of biological samples containing nucleic acids (i.e., impure nucleic acid samples), and dispense the set of biological samples into microfluidic cartridge 210 located in a molecular diagnostic module 130. The embodiment of the liquid handling system 100 is further configured to facilitate separation of a set of nucleic acids from the magnetic bead-samples, by dispensing a wash solution, a release solution, and/or air into the molecular diagnostic module 130, by the nozzle 149 coupled to the linear actuator 146, at appropriate stages, aspirate the set of nucleic acids from the molecular diagnostic module 130, combine the set of nucleic acids with a set of molecular diagnostic reagents, and dispense the set of nucleic acids combined with the set of molecular diagnostic reagents (i.e., set of nucleic acid-reagent mixtures) into the molecular diagnostic module 130 for further processing and analysis. Other embodiments of the liquid handling system 250 can be configured to perform alternative molecular diagnostic assay protocols and/or dispense and aspirate alternative fluids into and from other elements supporting a molecular diagnostic protocol.

The liquid handling system 250 is preferably an embodiment of the liquid handling system described in U.S. application Ser. No. 13/766,359 entitled "System and Method for Processing and Detecting Nucleic Acids" and filed on 13 Feb. 2013; however, the liquid handling system 250 can additionally or alternatively include any other suitable elements configured to facilitate delivery of biological samples, reagents, and gases to elements of the system 100.

1.4 System—Additional Elements

The system 100 can further comprise a controller coupled to at least one of the molecular diagnostic module 130 and the liquid handling system 250, and functions to facilitate automation of the system 100. In a variation wherein the controller is coupled to the molecular diagnostic module 130, the controller preferably functions to automate reception of a microfluidic cartridge, heating of biological samples within the molecular diagnostic module 130 and the detection chambers 213, occlusion of fluidic pathways 220 by the valve actuation subsystem 170, and analysis of a set of nucleic acid-reagent mixtures by the optical subsystem 280. In a variation wherein the controller is coupled to the liquid handling system 250, the controller preferably functions to automate aspiration, transfer, and delivery of fluids and/or gases to different elements of the system 100. Other variations of a controller can function to automate handling, transfer, and/or storage of other elements of the system 100, using a robotic arm or gantry or any other suitable element. Alternative combinations of the above variations can involve a single controller, or multiple controllers configured to perform all or a subset of the functions described above.

The system 100 can also further comprise a processor 290, which functions to receive and process data received from the optical subsystem 280 of the molecular diagnostic module 130. Preferably, the processor 290 is coupled to a user interface 295, which functions to display processed and/or unprocessed data produced by the system 100, settings of the system 100, information obtained from a tag reader, or any other appropriate information. Alternatively, the processor 290 is not coupled to a user interface 295, but comprises a connection configured to facilitate transfer of processed and/or unprocessed data produced by the system 100, settings of the system 100, or any other appropriate information to a device external to the system 100.

The system 100 can further comprise any other suitable element(s) as described in U.S. application Ser. No. 13/766,359 entitled "System and Method for Processing and Detecting Nucleic Acids" and filed on 13 Feb. 2013, or any other suitable element to facilitate reception or processing of biological samples. As a person skilled in the art will recognize from the previous detailed description and from the figures and claims, modifications and changes can be made the described embodiments of the system 100 without departing from the scope of the system 100.

2. Method for Processing and Detecting Nucleic Acids

Figure 11A:
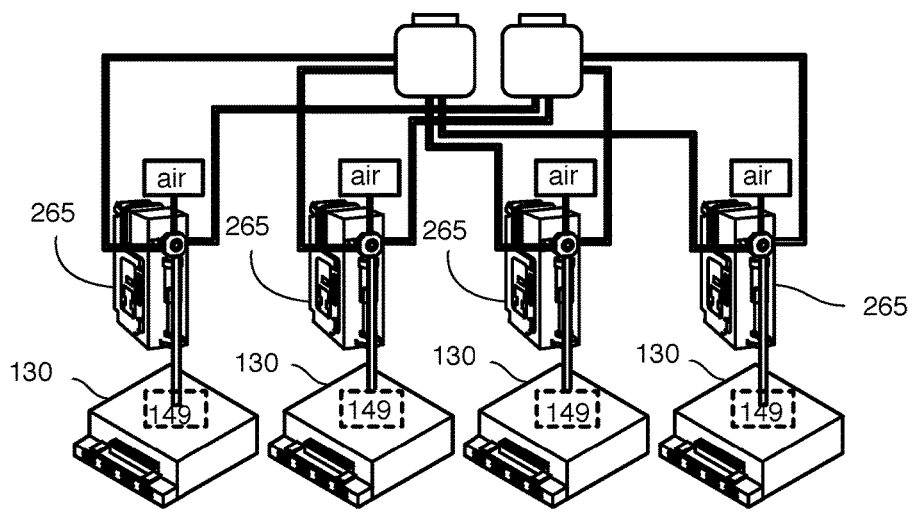
FIGS. 11A-11C depict an embodiment of a fluid handling system of a system for processing and detecting nucleic acids.
Figure 11B:
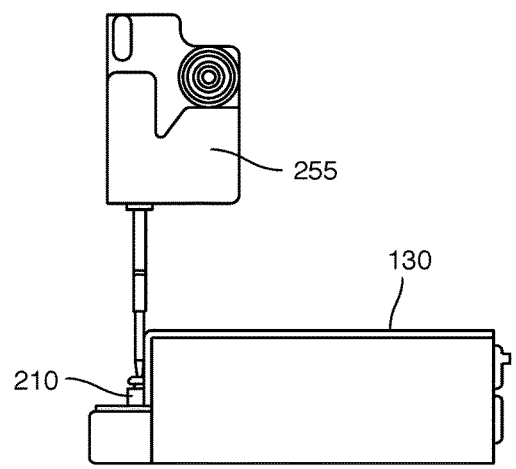
Figure 11C:
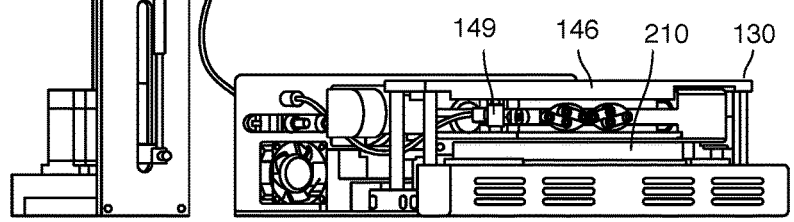
Figure 12:
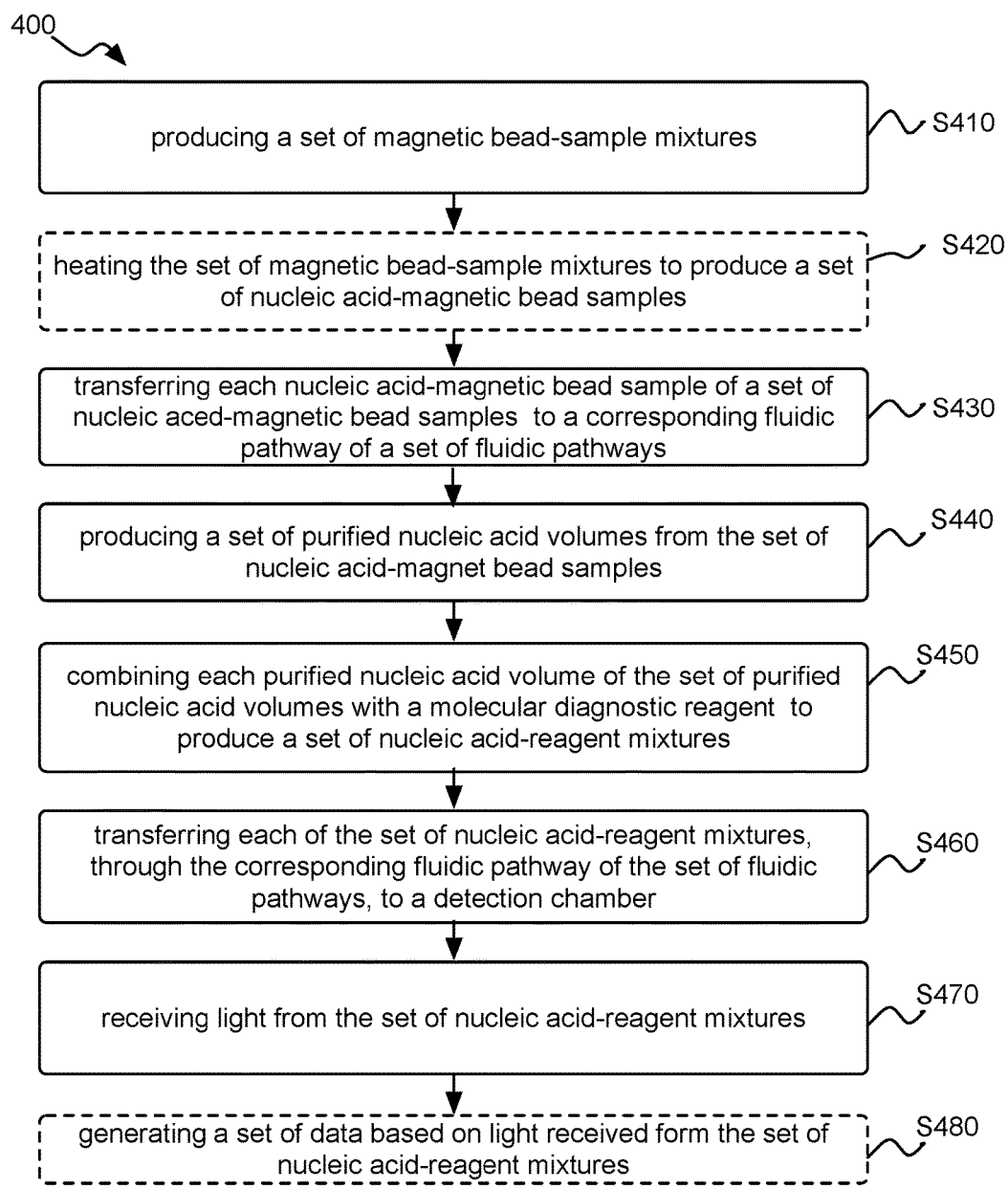
FIG. 12 depicts an embodiment of a method for processing and detecting nucleic acids.

As shown in FIG. 11, an embodiment of a method 400 for processing and detecting nucleic acids from a set of biological samples comprises: producing a set of magnetic bead-sample mixtures from the set of biological samples S410; heating the set of magnetic bead-sample mixtures to produce a set of nucleic acid-magnetic bead samples S420; transferring each nucleic acid-magnetic bead sample of the set of nucleic acid-magnetic bead samples to a corresponding fluidic pathway of a set of fluidic pathways S430; producing a set of nucleic acid volumes from the set of nucleic acid-magnetic bead samples S440; combining each nucleic acid volume of the set of nucleic acid volumes with a molecular diagnostic reagent of a set of molecular diagnostic reagents to produce a set of nucleic acid-reagent mixtures S450; transferring each of the set of nucleic acid-reagent mixtures, through the corresponding fluidic pathway of the set of fluidic pathways, to a detection chamber of a set of detection chambers S460; and receiving light from the set of nucleic acid-reagent mixtures S470. The method 400 can further include generating a set of data based on light received form the set of nucleic acid-reagent mixtures S480. The method 400 functions to isolate and extract a set of nucleic acid volumes from a biological sample, and to facilitate analysis of the nucleic acid volumes according to at least one molecular diagnostic protocol.

The method 400 is preferably implemented at least in part at an embodiment of the system 100 described in Section 1 above; however, the method 400 can additionally or alternatively be implemented at any other suitable system configured to process and detect nucleic acids from a set of biological samples. Preferably, the method 400 is implemented, at least in part, as described in U.S. application Ser. No. 13/766,377 entitled "System and Method for Processing and Detecting Nucleic Acids" and filed on 13 Feb. 2013, and U.S. application Ser. No. 14/060,214 entitled "Method and Materials for Isolation of Nucleic Acid Materials" and filed on 22 Oct. 2013, which are both incorporated herein in their entirety by this reference; however, the method 400 can additionally or alternatively be implemented in any other suitable manner.

Embodiments of the method 400 and variations thereof can be embodied and/or implemented at least in part by a machine configured to receive a computer-readable medium storing computer-readable instructions. The instructions are preferably executed by computer-executable components preferably integrated with the system 100 and one or more portions of the processor 273 and/or the controller 272. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for processing and detecting nucleic acids using a cartridge with a fluidic pathway, the system comprising:
 a cartridge platform configured to receive the cartridge, the cartridge platform comprising an access region configured to align with the fluidic pathway;
 a valve actuation subsystem comprising:
  a pin comprising a first end, a second end, and a displacement region, the pin actuatable along a displacement axis extending through the first end, the second end, and the access region;
  a spring, coupled to the displacement region of the pin, that biases the pin along the displacement axis; and
  an actuation substrate comprising a groove and a protrusion, the actuation substrate translatable along an actuation axis perpendicular to the displacement axis;
 wherein the system is operable between:
  a closed configuration, wherein the groove is aligned with the displacement region and the first end of the pin extends through the access region; and
  an open configuration, wherein the protrusion is aligned with the displacement region and the first end of the pin is displaced away from the access region.

2. The system of claim 1, wherein the cartridge comprises a set of fluidic pathways, wherein the fluidic pathway is one of the set of fluidic pathways, the system further comprising a magnet, arranged inferior the cartridge platform, that applies a magnetic field spanning at least three fluidic pathways of the set of fluidic pathways.

3. The system of claim 1, further comprising an optical subsystem, arranged superior the cartridge platform, that comprises a set of units, wherein each unit includes an excitation filter, an emission filter, a photodetector aligned with the emission filter, and a dichroic mirror.

4. The system of claim 1, further comprising a linear actuator, mounted to the cartridge platform, that actuates the cartridge platform along the displacement axis.

5. The system of claim 1, further comprising the cartridge, wherein the cartridge includes a set of sample port-reagent port pairs, a fluid port, a set of detection chambers, a waste chamber, and a set of fluidic pathways, wherein the fluidic pathway is one of the set of fluidic pathways, wherein each fluidic pathway is coupled to a sample port-reagent port pair of the set of sample port-reagent port pairs, the fluid port, and a detection chamber of the set of detection chambers, wherein the fluidic pathway is occluded by the pin in the closed configuration.

6. The system of claim 1, wherein the valve actuation subsystem further comprises a pin housing surrounding the pin, the pin housing comprising a stop region, proximal the displacement region, that halts pin displacement toward the access region along the displacement axis.

7. The system of claim 1, wherein the valve actuation subsystem further comprises a substrate actuator that displaces the actuation substrate along the actuation axis between a first substrate position and a second substrate position along the actuation axis, wherein the actuation substrate is in the first substrate position when the system is in the closed configuration, and is in the second substrate position when the system is in the open configuration.

8. The system of claim 1, wherein the displacement region of the pin is arranged proximal the second end, between the first end and second end, and comprises a slot defined along a length of the pin.

9. The system of claim 8, wherein the actuation substrate passes through the slot, wherein the groove and the protrusion are defined along a face of the actuation substrate parallel the actuation axis.

10. The system of claim 9:
 wherein the spring is mounted to the second end of the pin and biases the pin toward the access region;
 wherein the slot further comprises a pin protrusion extending from an end of the slot proximal the second end; and
 wherein the face of the actuation substrate is proximal the pin protrusion.

11. The system of claim 10, wherein the protrusion and the pin protrusion each comprise a convex profile.

12. A system for processing a biological sample with a cartridge comprising a set of fluidic pathways, each fluidic pathway comprising an occlusion region, the system comprising:
 a pin comprising a first end and a second end, the pin actuatable along a displacement axis between a first pin position and a second pin position, wherein the first end of the pin occludes the occlusion region of a fluidic pathway of the cartridge in the first pin position, and the first end of the pin does not occlude the access region of the fluidic pathway of the cartridge in the second pin position;
 an actuation substrate comprising a first substrate feature and a second substrate feature, the actuation substrate actuatable between a first substrate position and a second substrate position; and
 a pin-substrate interface aligning and energetically coupling at least one of the first substrate feature and the second substrate feature with the second end of the pin;
 wherein the system is operable between:
  a closed state, wherein the actuation substrate is in the first substrate position, the first substrate feature is aligned with the second end of the pin at the pin-substrate interface, and the pin is in the first pin position; and
  an open state, wherein the actuation substrate is in the second substrate position, the second substrate feature aligned with the second end of the pin at the pin-substrate interface, and the pin is in the second pin position.

13. The system of claim 12, wherein the actuation substrate is actuatable between the first substrate position and the second substrate position along an actuation axis perpendicular to the displacement axis, the system further comprising an actuator coupled to the actuation substrate that actuates the actuation substrate along the actuation axis.

14. The system of claim 12, wherein the first substrate feature applies one of a neutral or negative force to the pin at the pin-substrate interface, and the second substrate feature applies a positive force to the pin at the pin-substrate interface.

15. The system of claim 14, wherein the first substrate feature comprises a groove, and the second substrate feature comprises a protrusion.

16. The system of claim 15, wherein the pin-substrate interface comprises a spring, coupled to the second end of the pin, that applies a spring force opposing the positive force and biases the pin towards the first pin position along the displacement axis.

17. The system of claim 16, wherein the pin-substrate interface further comprises a slot, defined by the pin, proximal the second end.

18. The system of claim 17, wherein the actuation substrate is actuatable between the first substrate position and the second substrate position along an actuation axis perpendicular to the displacement axis, wherein the actuation substrate extends through the slot parallel the actuation axis, wherein the groove and the protrusion are defined along a face of the actuation substrate.

19. The system of claim 18,
wherein the groove and protrusion are defined along an inferior face of the actuation substrate;
wherein the slot comprises a pin protrusion at an inferior end of the slot; and
wherein the spring is mounted to the second end of the pin, inferior the slot.

20. The system of claim 12, further comprising:
a cartridge platform configured to receive the cartridge, wherein the valve actuation subsystem is arranged inferior the cartridge platform;
a magnet, arranged inferior the cartridge platform, that applies a magnetic field spanning at least three fluidic pathways of the set of fluidic pathways;
an optical subsystem, arranged superior the cartridge platform, that comprises an excitation filter, an emission filter, a photodetector aligned with the emission filter, and a dichroic mirror optically connected to the emission filter, cartridge, and the photodetector; and
a linear actuator, mounted to the cartridge platform, that actuates the cartridge platform along the displacement axis.

* * * * *